United States Patent [19]

Larkin

[11] Patent Number: 4,614,267

[45] Date of Patent: Sep. 30, 1986

[54] DUAL COMPARTMENTED CONTAINER

[75] Inventor: Mark E. Larkin, Lindenhurst, Ill.

[73] Assignee: Abbott Laboratories, North Chicago, Ill.

[21] Appl. No.: 565,126

[22] Filed: Dec. 23, 1983

Related U.S. Application Data

[63] Continuation-in-part of Ser. No. 470,105, Feb. 28, 1983, abandoned.

[51] Int. Cl.[4] ........................ A61M 5/14; B65D 25/08

[52] U.S. Cl. .................................... 206/221; 206/219; 215/DIG. 8; 383/96; 493/186; 604/415

[58] Field of Search ................................ 206/219–222, 206/216, 568, 438; 215/6, 10, DIG. 8; 604/56, 82, 87, 92, 408–410, 415, 416; 383/66, 67, 93, 96; 493/186, 212

[56] References Cited

U.S. PATENT DOCUMENTS

| | | | |
|---|---|---|---|
| 708,264 | 9/1902 | Sherman . | |
| 806,090 | 12/1905 | Allenberg | 383/38 |
| 2,176,923 | 10/1939 | Nitardy . | |
| 2,721,552 | 10/1955 | Nosik . | |
| 2,746,632 | 5/1956 | Bramming . | |
| 2,764,983 | 10/1956 | Barasch et al. . | |
| 2,781,141 | 2/1957 | Lucien . | |
| 2,969,792 | 1/1961 | Milton . | |
| 3,082,895 | 3/1963 | Leslie-Smith | 214/364 |
| 3,239,429 | 3/1966 | Menolasino et al. . | |
| 3,290,017 | 12/1966 | Davies et al. . | |
| 3,376,866 | 4/1968 | Ogle . | |
| 3,439,823 | 4/1969 | Morane . | |
| 3,532,254 | 10/1970 | Burke . | |
| 3,542,023 | 11/1970 | Ogle . | |
| 3,684,455 | 8/1972 | Vacirca et al. . | |
| 3,696,919 | 10/1972 | Miles . | |
| 3,731,853 | 5/1973 | Baumann et al. . | |
| 3,796,303 | 3/1974 | Allet-Coche . | |
| 3,840,136 | 10/1974 | Lanfranconi et al. . | |
| 3,870,147 | 3/1975 | Orth . | |
| 3,915,212 | 10/1975 | Bujan et al. . | |
| 3,945,382 | 3/1976 | Ogle . | |
| 3,970,207 | 7/1976 | Faulstich . | |
| 4,024,952 | 5/1977 | Leitz . | |
| 4,102,451 | 7/1978 | Clarke et al. . | |
| 4,161,178 | 7/1979 | Genese . | |
| 4,181,140 | 1/1980 | Bayham et al. . | |
| 4,187,893 | 2/1980 | Bujan . | |
| 4,221,291 | 9/1980 | Hunt . | |
| 4,363,416 | 12/1982 | Loughmiller | 215/364 |
| 4,396,383 | 8/1983 | Hart | 604/410 |
| 4,403,992 | 9/1983 | Bertellini et al. . | |
| 4,410,321 | 10/1983 | Pearson et al. | 604/410 |
| 4,458,733 | 7/1984 | Lyons | 206/219 |
| 4,465,488 | 8/1984 | Richmond et al. . | |
| 4,467,588 | 8/1984 | Carveth | 604/410 |
| 4,515,586 | 5/1985 | Mendenhall et al. . | |
| 4,550,825 | 11/1985 | Sutryn et al. . | |

FOREIGN PATENT DOCUMENTS

| | | | |
|---|---|---|---|
| 1486622 | 7/1969 | Fed. Rep. of Germany | 215/6 |
| 2529341 | 1/1977 | Fed. Rep. of Germany . | |
| 1180102 | 6/1959 | France . | |
| 0094886 | 1/1970 | France . | |
| 2500814 | 2/1981 | France . | |
| 1033807 | 8/1979 | Italy . | |
| 364073 | 10/1962 | Switzerland . | |

*Primary Examiner*—William Price
*Assistant Examiner*—Jimmy G. Foster
*Attorney, Agent, or Firm*—Neuman, Williams, Anderson & Olson

[57] ABSTRACT

A stoppered vial containing a medicament is secured through the edge of a flexible container. Mixing of the medicament in the vial with the contents of the flexible container is accomplished by removing the stopper from the vial by manipulation through the sides of the flexible container. In one embodiment, the stoppered vial is mounted through and in the edge of the flexible container and in another embodiment the flexible container has a port which will receive the stoppered vial therein in a secure manner.

86 Claims, 29 Drawing Figures

DUAL COMPARTMENTED CONTAINER

CROSS-REFERENCE TO RELATED APPLICATIONS

This application is a continuation-in-part of application Ser. No. 470,105, now abandoned filed Feb. 28, 1983 and is commonly assigned.

BACKGROUND OF THE INVENTION

This invention relates to a manually operated dual compartmented container having the means to intermix the contents of the two compartments from outside the container. More particularly this invention relates to an additive container which is made a part of a flexible container holding a standard diluent such as normal saline solution, dextrose or water. In this manner a predetermined amount of medicament either in powdered or liquid form may be added to a diluent by activation of the additive transfer device and the resulting solution administered intravenously to a patient.

Devices providing separate compartments in a single container for separately enclosing different components in such a way that they may be later intermixed are described in U.S. Pat. No. 2,176,923 to Nitardy, U.S. Pat. No. 3,290,017 to Davies et al. and U.S. Pat. No. 3,532,254 to Burke et al. These devices are deficient in not being able to maintain an effective seal between the two components to be intermixed. Additionally the barrier between the chambers does not adequately withstand for rigors of handling and shipping leading to premature removal or leakage of moisture into the dry medicament. For containers used in health care situations, sterility must be maintained. While simple in configuration the arrangement of parts in the devices found in the prior art makes them difficult to sterilize unless the entire device is assembled in a totally sterile environment. Such manufacture is exceedingly expensive.

Nowhere in the prior art is there available a dual compartmented container for storing and transferring a medicament from a vial to a solution container wherein a medicament vial is assembled and formed originally as part of the edge of a flexible container or later received and secured therethrough. Nor does the prior art provide an additive container transfer mechanism within a dual compartmented container that provides the opportunity for multiple moisture barrier seals in the same container for leak-free separation of the medicament and the diluent before mixing. The prior art is specifically directed to single plug type devices for temporarily sealing the contents of one compartment from the other compartment in a single container system. The use of a stopper and vial combination in conjunction with a cover or stopper removal means and sleeve provides multiple opportunities for establishing multiple fluid tight or moisture barrier seals between the two compartments.

It is therefore an advantage of the present invention to afford a manually operated dual compartmented container not subject to the aforementioned and the other disadvantages of the prior art.

It is another advantage of the present invention to provide a manually operable dual compartmented container that is substantially chemically inert, lightweight and exceedingly compact.

It is still another advantage of the present invention to provide a manually operable dual-compartmented container that will afford rapid intermixing of the contents of the two containers. Other objects and advantages of the present invention will become apparent as the description proceeds.

SUMMARY OF THE INVENTION

The foregoing advantages are accomplished and the shortcomings of the prior art are overcome by the present manually operated dual compartmented container wherein the wall means either in the form of an edge portion or a tubular port of a flexible outer container provides a means for securing a stoppered container vial with stopper removal means positioned in the inside of the outer container. The fluid contents of the vial and the flexible container may be mixed by manipulation from the exterior of the flexible bag which effects removal of the stopper by means of the stopper removal means from the vial inside the outer container. Accordingly, fluid communication is provided between the two compartments for mixing of the fluid contents of the compartments.

DESCRIPTION OF THE DRAWINGS

A better understanding of the manually operated dual compartmented container will be had by reference to the drawings wherein.

DESCRIPTION OF THE PREFERRED EMBODIMENTS

Figure 1:
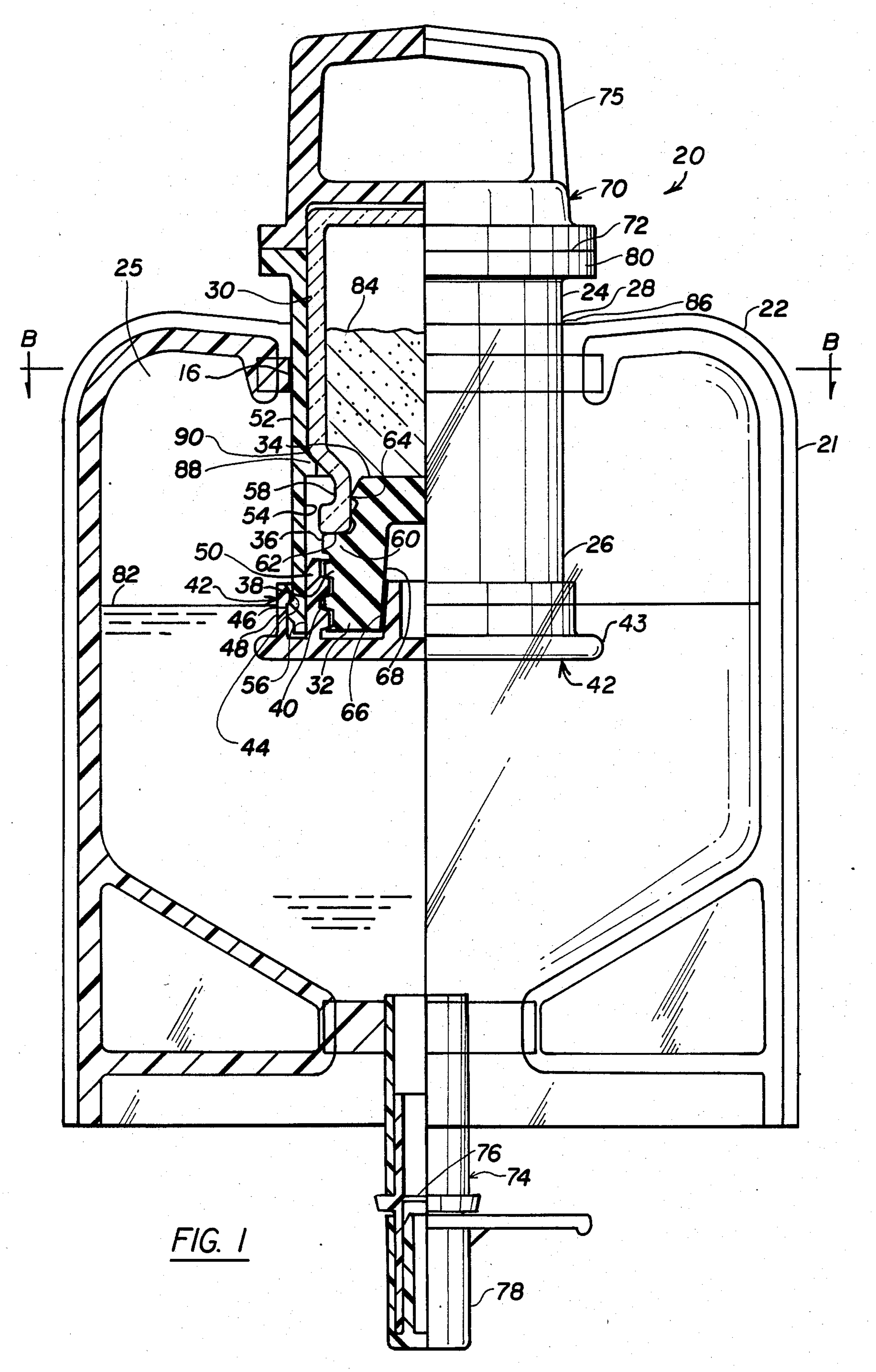
FIG. 1 is a view in front elevation of the dual compartmented container with portions shown in vertical section.
Figure 1A:
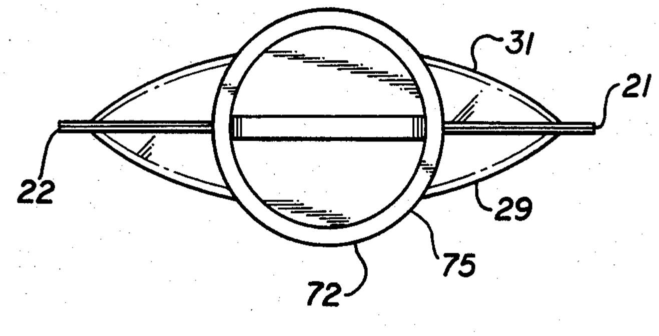
FIG. 1A is a top view of the dual compartmented container shown in FIG. 1.

Proceeding to a detailed description of one embodiment of the invention, the manually operated dual compartmented container generally 20 is shown in FIGS. 1–4. It is adapted to be used with a flexible container 22 formed from two opposing sheets of flexible material that have been joined and sealed at the edges 21. Container 22 is constructed to provide a fluid tight compartment 25 for diluent 82 between opposing side walls such as 29 and 31. Sealed through an opening 86 in the sealed edges 21 of the flexible container by means of mandrel seal 16 is a sleeve 24 which has a portion 26 within the compartment 25 of the flexible container and portion 28 outside the edges 21 of the flexible container 22. It will be appreciated that as the flexible container is formed from two opposing sheets of plastic material, sleeve 24 will in effect be placed between the opposing edges such as shown at 86.

Disposed within the sleeve in a tight fitting manner is a glass vial 30 containing medicament 84 which is shown in powdered form but may also be a liquid. Positioning the vial 30 within sleeve 24 is inwardly facing annular ridge 88 which contacts an angled wall portion 90 of vial 30. The vial 30 is sealed with a stopper 32 which has a reduced portion 34, fitting within the neck 58 of the vial 30 and an expanded portion 36 which extends from the neck 58 of the vial 30. On the expanded portion 36 of the stopper 32 extending from the neck 58 of the vial 30 are external threads 38 which are compatible with internal threads 40 formed on annulus 50 which extends from cover 42. The cover 42 is thereby threadably engaged with the stopper 32 and also engaged with sleeve 24 by means of an annular lip 44 formed on the skirt portion 48. Annular lip 44 is constructed to snap over outwardly facing annular ridge 46 extending from the exterior wall 52 of the sleeve 24. A first fluid tight seal is thus formed at the contacting surfaces on the inside of the skirt 48 and the exterior of sleeve 24. A second fluid tight seal is formed on the interior wall 54 of sleeve 24 where it contacts the flat portion 56 of annulus 50 which extends from cover 42. Additional fluid tight seals are provided between vial rim or finish 62 and shoulder 60 on stopper 32 and between the throat 64 of vial 30 and the contacting edge of reduced portion 34 of stopper 32 which extends into the neck 58 of the vial 30. For ease of manufacture and to prevent distortion, cover alignment annulus 66 is placed into recess 68 formed within stopper 32.

The outwardly extending portion of vial 30 may be covered by a cap structure generally 70 which includes flange 72 for sealing to flange 80 formed on the portion 28 of sleeve 24 external to flexible container 22. A hanger 75 is integrally formed as a portion of cap 70 to facilitate hanging the dual compartmented container such as when made part of a standard I.V. system (not shown). Shown on the bottom of flexible container 22 is a port generally 74 which may be used to fill the flexible container 22 with liquid diluent 82 or to administer the mixture 83 of the fluid 82 and the medicament 84 contained within the vial 30. The port 74 may also include the usual diaphragm 76 and a cap 78.

FIGS. 5–13 depict several embodiments wherein the same reference numbers have been employed to designate components having the same function, construction and relative location as in the embodiment of FIG. 1. It will be appreciated that in all of the embodiments the vial or inner container is sealed with the stoppered portion within the outer container.

Figure 5:
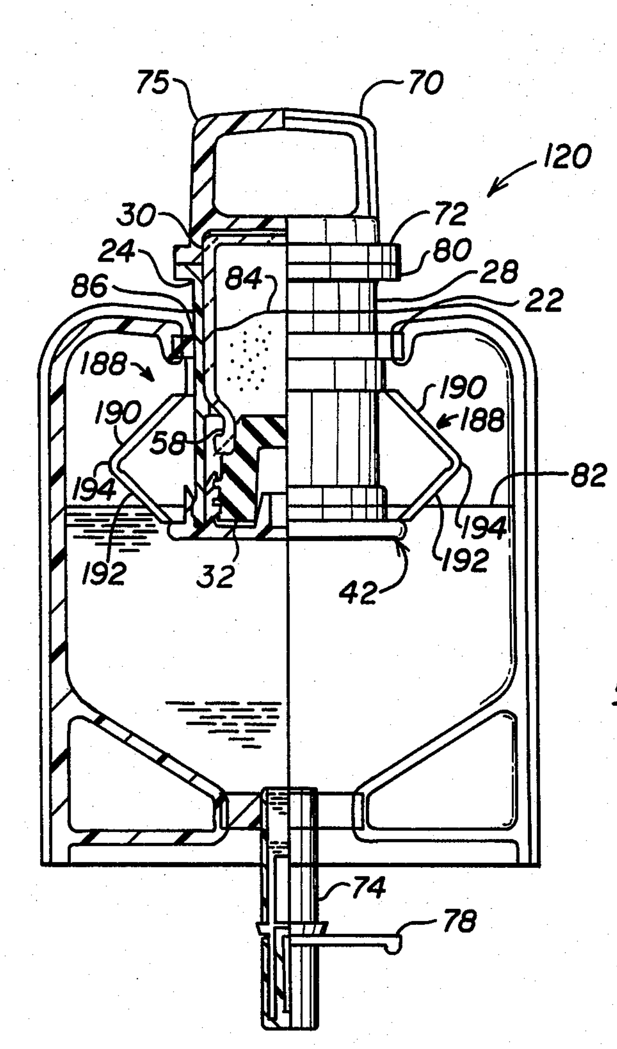
FIG. 5 is a view similar to FIG. 1 with FIG. 5A being a partial view of FIG. 5 illustrating an additional embodiment wherein toggle means are employed between the sleeve and the cover for activation.
Figure 5A:
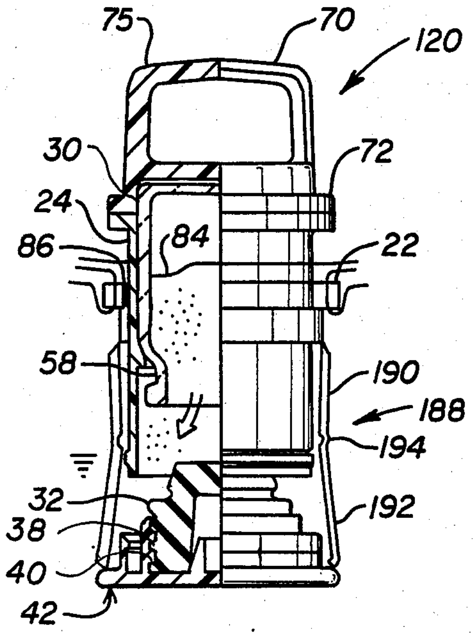

FIGS. 5 and 5A depict a first alternative embodiment generally 120 wherein connecting the cover 42 with the sleeve 24 is a toggle means generally 188 located on either side of the sleeve 24. The toggle means 188 has a pair of arm members 190 and 192 joined by a flexible portion 194 on either side of sleeve 24. When the toggle means 188 is flexed outward as shown in FIG. 5 the stopper 32 and cover 42 are in fluid sealed relationship with respect to vial 30 and sleeve 24. When extended or flexed inward as in FIG. 5A the toggle means 188 allows the cover 42 and stopper 32 combination to move away from the vial 30 so as to allow passage of the medicament 84 from within vial 30 to the diluent 82 within flexible container 22.

Figure 6:
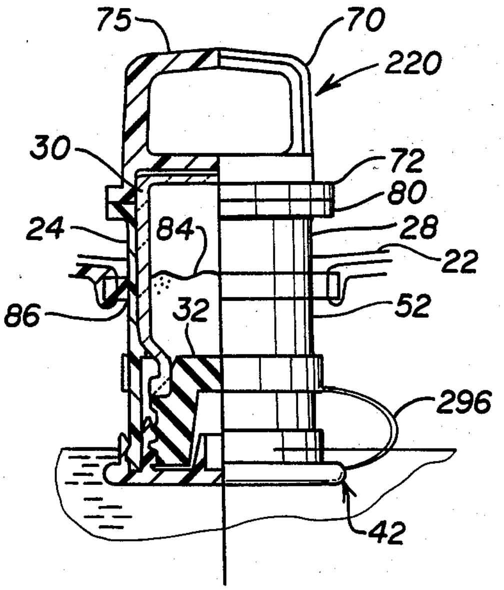
FIGS. 6 and 6A are views similar to FIG. 5A showing a further embodiment wherein strap means are employed between the sleeve and the cover.
Figure 6A:
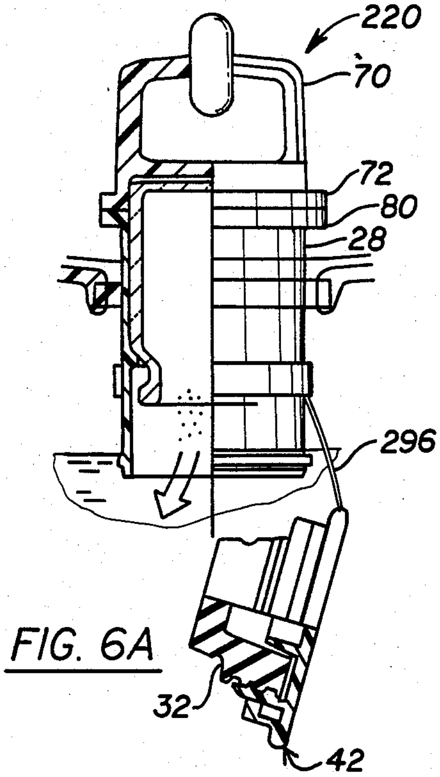

FIGS. 6 and 6A depict a second alternative embodiment generally 220 wherein connecting the cover 42 to the sleeve 24 is a strap 296. The strap 296 allows the stopper 32 and cover 42 combination to be in fluid sealed relationship with the vial 30 and sleeve 24, respectively, but allows the stopper 32 and cover 42 combination to swing away from the sleeve 24 and vial 30 as one unit when it is desired to intermix the medicament 84 in the vial 30 and the diluent 82 in the flexible container 22 as shown in FIG. 6A.

Figure 7:
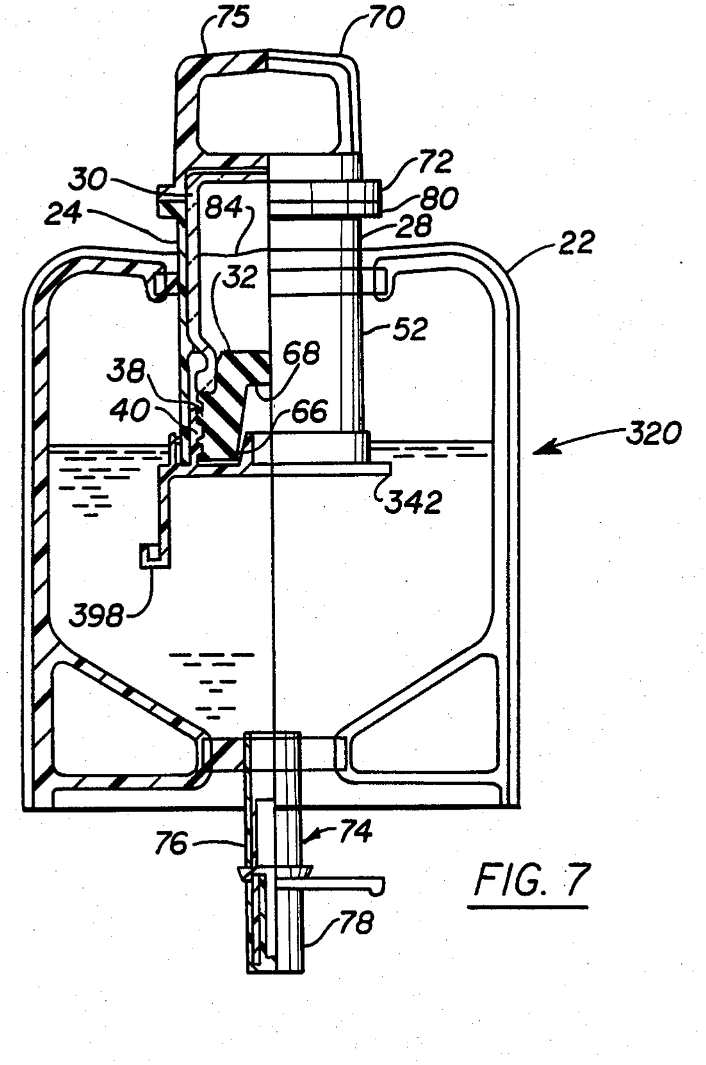
FIG. 7 is a view similar to FIG. 1 illustrating yet another embodiment wherein tab means are employed in conjunction with the cover.

FIG. 7 depicts a third alternative embodiment generally 320 wherein there is attached to the cover 342 a tab means 398. Tab means 398 may be gripped from outside the flexible sides such as 29 of container 22 and used to assist the user in removing the cover 342 and stopper 32 combination from the sleeve 24 and vial 30 respectively.

Figure 8:
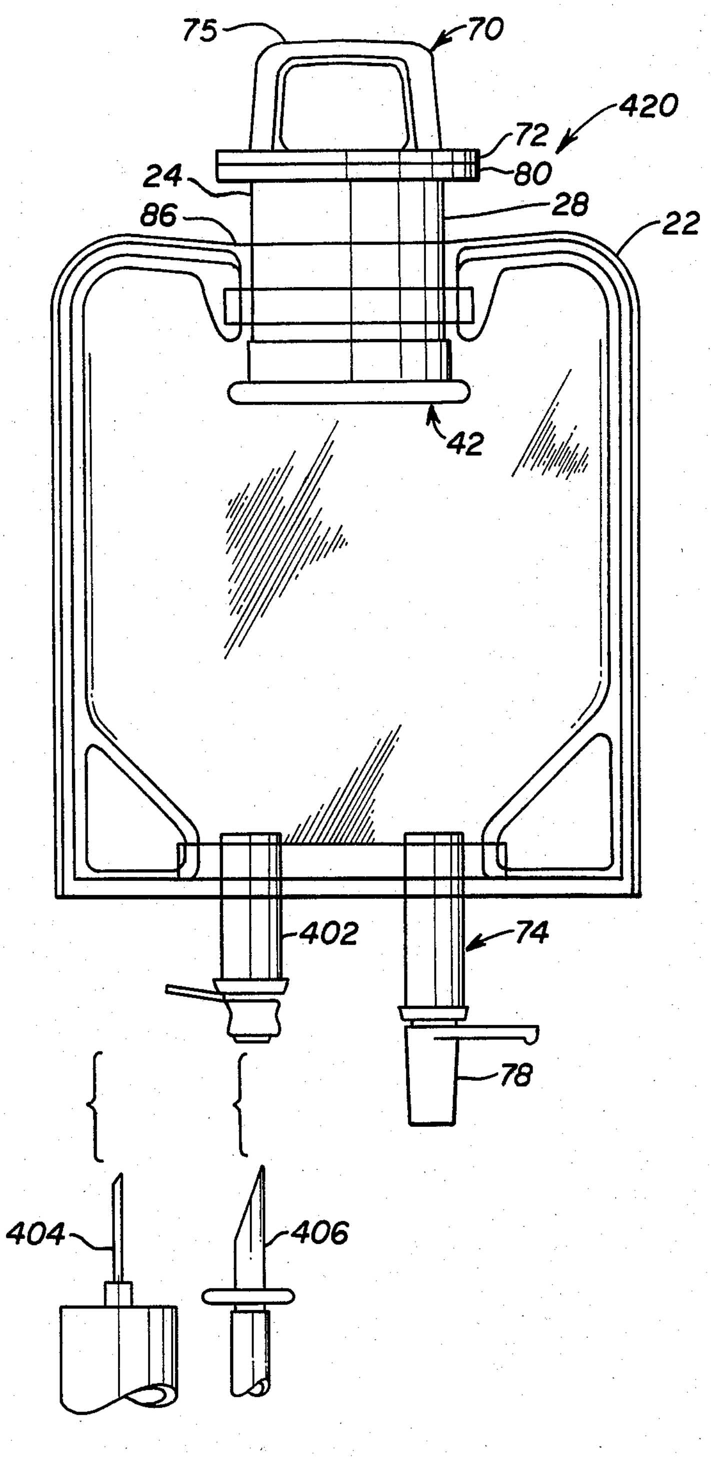
FIG. 8 is a view in front elevation of the dual compartmented container as shown in FIG. 1 employing an additional port means adaptable for use with a syringe or a transfer spike.

FIG. 8 depicts a fourth alternative embodiment generally 420 wherein the flexible container 22 includes an additional port means 402 which may be used for the insertion of a syringe cannula 404 or spike 406 to add diluent to an empty container 22, to sample the mixture after activation of the vial by removal of cover 42, or to attach to an I.V. administration set.

Figure 9:
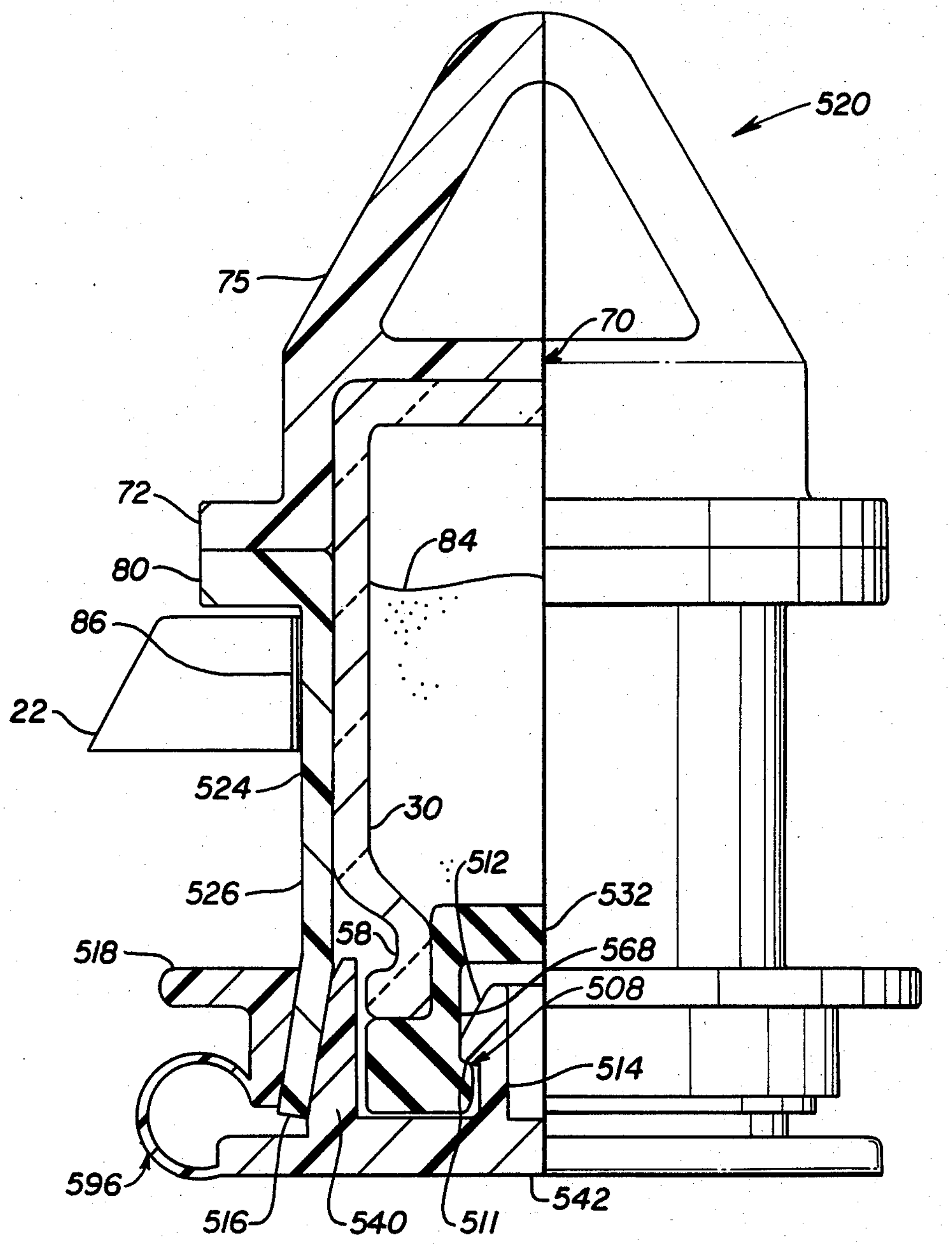
FIG. 9 is a partial view similar to FIG. 1 of the dual compartmented container illustrating yet another embodiment wherein handle means and a tapered strap are employed in conjunction with the cover for activation of the vial.

FIG. 9 depicts a fifth alternative embodiment generally 520 wherein a central latch means generally 508 is disposed within a recess 568 located within the central portion of stopper 532. It is used to secure the cover 542 to the stopper 532 instead of the threadable engagement 38, 40 shown in FIGS. 1, 5, 6 and 7. Recess 568 has an inward facing lip 511 around its outer edge for engagement with projection 512 of latch arm 514 from the cover 542 which extends into the recess 568 in the stopper 532. The lower portion 526 of sleeve 524 within flexible bag 22 terminates in an outwardly tapering portion 516 which matches the taper of protrusion 540 from cover 542. Flanged tapered ring 518 slides down sleeve 524 and sandwiches outwardly tapering portion 516 against protrusion 524. Strap 596 connects the flanged tapered ring 518 to the base of cover 542. Accordingly, flanged tapered ring 518 and latch means 508 act together to hold cover 542 in place on the sleeve 524 and in contact with stopper 532.

Figure 10:
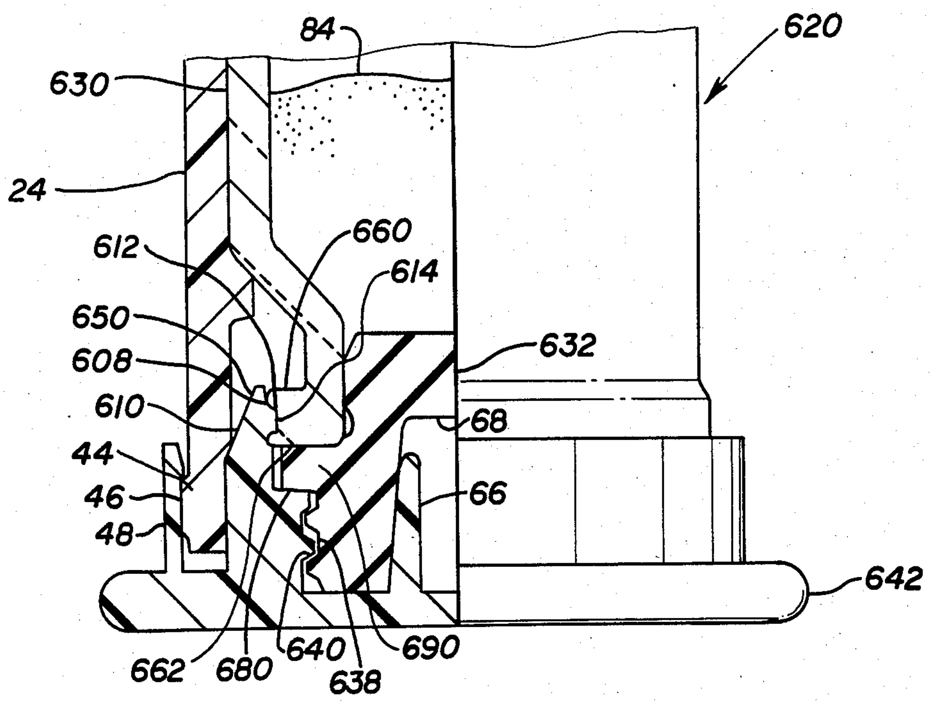
FIG. 10 is a partial view similar to FIG. 9 wherein an additional sealing means between the cover and vial are illustrated.

FIG. 10 depicts a sixth alternative embodiment generally 620 wherein a second additional rotatable engagement means 608 is used to secure the cover 642 not only to the rubber stopper 632 and the sleeve 24 but also to the vial 630. Annulus 650 is formed on cover 642 to include both internal screw threads 640 and an extended portion 610 which carries a projecting portion 612 of second rotatable engagement means 608. Projecting portion 612 operatively engages an internally threaded portion 614 formed in the side of the outwardly extending annular lip 660 around the mouth or finish of vial 630. A compression ring 690 is formed on stopper 632 inwardly of external threads 638. An additional seal is formed by the force on compression ring 690 from annular shoulder 680 of cover 642 directed toward vial finish 662.

Figure 11:
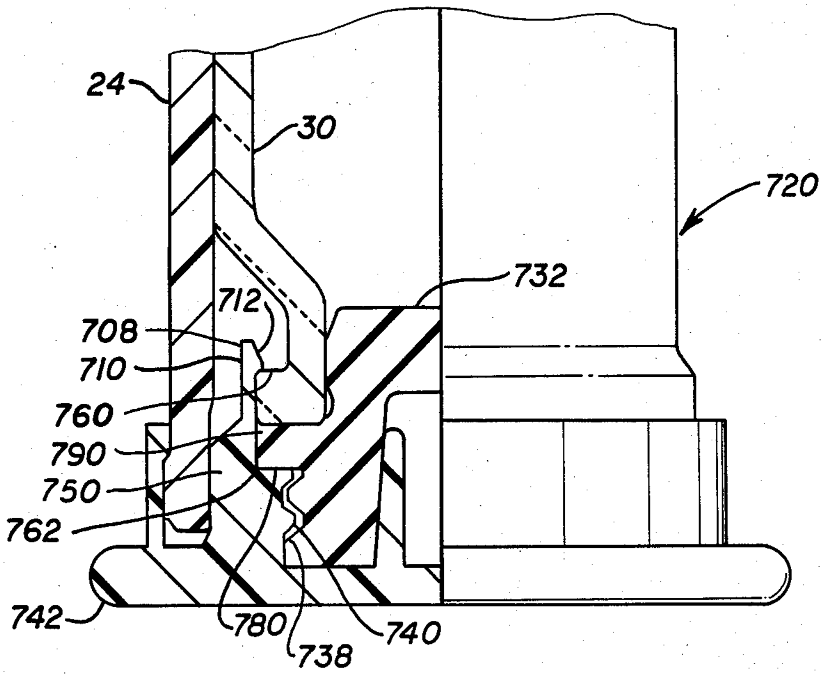
FIG. 11 is a view similar to FIG. 10 wherein an alternative additional sealing means between the cover and vial are shown for a dual compartmented container.

FIG. 11 depicts a seventh alternative embodiment generally 720 wherein additional detachable sealing means generally 708 are used to secure the cover 742 not only to the rubber stopper 732 and the sleeve 24 but also to the vial 30. Annulus 750 is formed in cover 742 to include both internal screw threads 740 and an extended latch portion 710. Extended latch portion 710 carries a projection 712 which engages the underside of the outwardly extending annular lip 760 around the mouth of the vial 30 in a snap-fit manner. A compression ring 790 is formed on stopper 732 inwardly of external threads 738. An additional fluid-tight seal is formed by the force on compression ring 790 from shoulder 780 directed toward finish 762.

Figure 12:
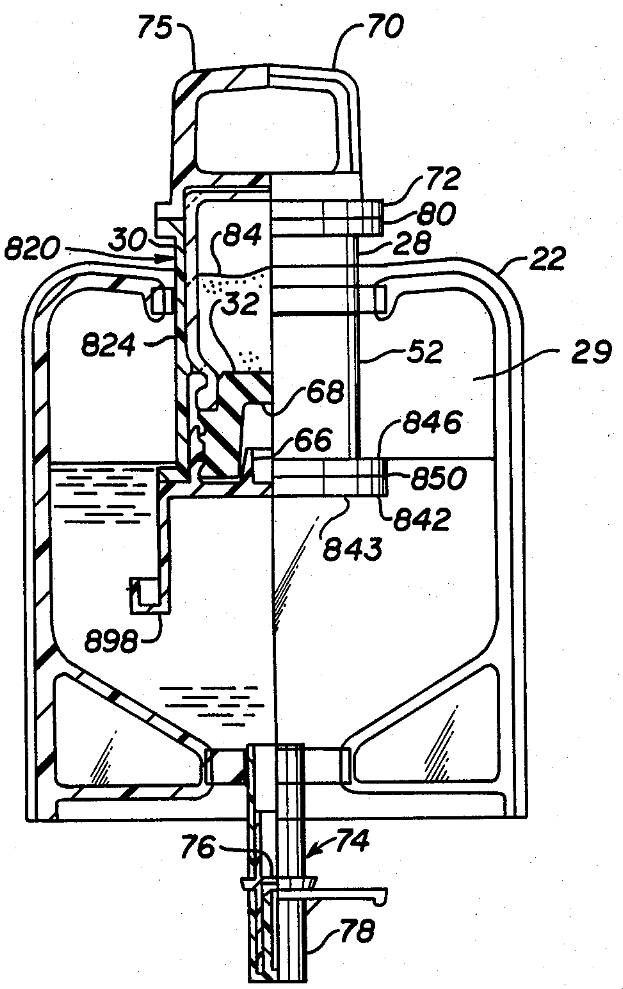
FIG. 12 is a view similar to FIG. 1 of yet another embodiment wherein a flange weld is illustrated to attach the cover to the sleeve.

FIG. 12 depicts an eighth alternative embodiment generally 820 wherein flange means 846 is formed on the bottom portion of sleeve 824 which extends into flexible container 22. Cover 842 is attached to stopper 32 as illustrated in FIG. 1 but is secured to sleeve 824 by a weak weld such as indicated at 850 where flange portion 843 of cover 842 meets flange means 846. Tab means 898 is used to peel cover 842 from sleeve 824 on activation of the device.

Figure 13:
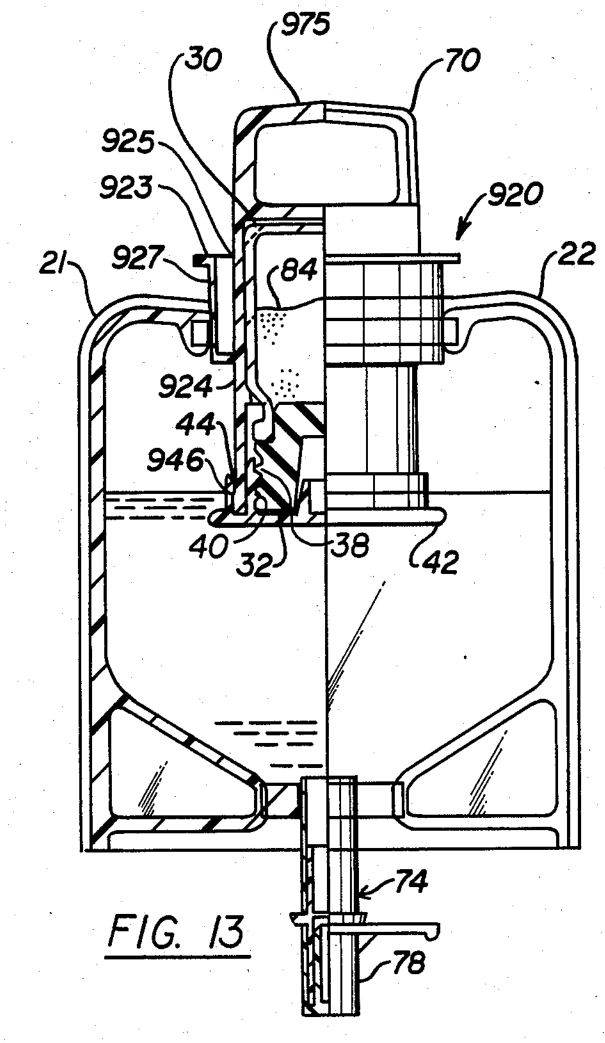
FIG. 13 is a view similar to FIG. 12 of still another embodiment of a dual compartmented container wherein the sleeve is depicted with an additional casing for sealing in the flexible container.

FIG. 13 depicts a ninth alternative embodiment generally 920 wherein a closed end vial receiving casing generally 923 is sealed within the edge 21 of flexible container 22. Hanger means 975 is attached to the end 925 of vial receiving casing 923. A double wall portion 927 provides a space for an internal mandrel support surface to facilitate RF welding of bag 22 to vial receiving casing 923.

FIGS. 14–25 illustrate alternative embodiments of this invention wherein the additive vial such as 30 will be filled and packaged separately from flexible container 22. Accordingly, rather than being sealed through the container wall by means of a sleeve 24 it will instead be secured through the wall means by reception in and interconnection in a port 14. This interconnection would be effected, for example, in a hospital pharmacy. In describing embodiments 10, 110, 210, 310, 410 and 510, the same components will be referred to by the same numbers as previously described.

Figure 14:
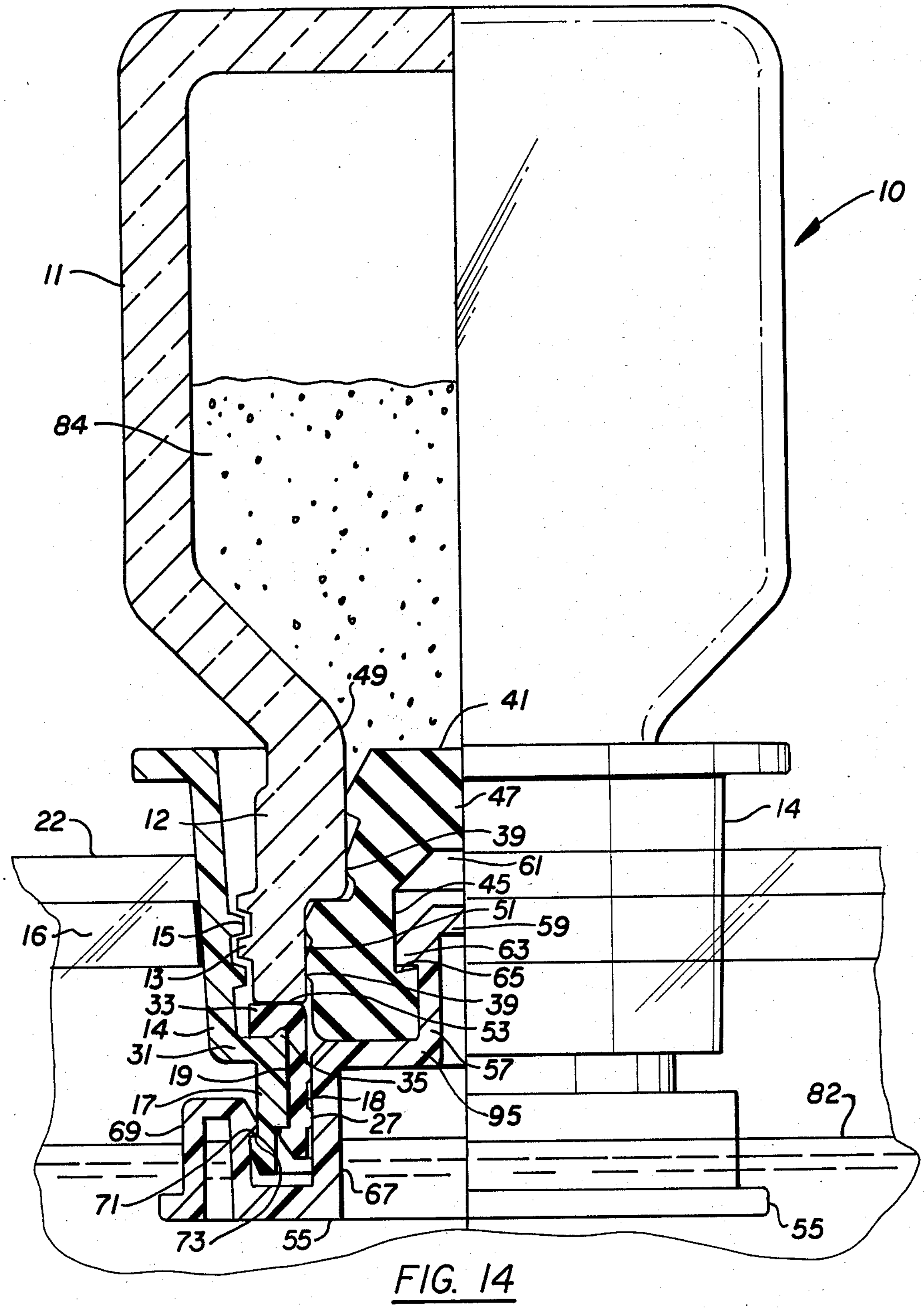
FIG. 14 is a view partially in side elevation and partially in vertical section of an alternative embodiment of this invention wherein the medicament vial is threadably received in the flexible container.

Referring to FIG. 14, it will be seen that embodiment generally 10 includes a vial 11 having the usual neck portion 12 with threads 13 extending therefrom. Complementary threads 15 extend internally from port 14 which is mandrel sealed at 16 to flexible container 22. A gasket 18 which is substantially J-shaped in cross section has a leg portion 33 for seating on transverse shoulder 31 of port 14 and for sealing with vial finish 51. Gasket 18 is further secured in port 14 through recess 19 in gasket 18 for positioning over annular flange 17. Annular or ring portions 27 extend from gasket 18 for sealable engagement with cover 55 and particularly annular wall 67. Cover 55 includes a latch portion 69 for frictional engagement and seating on shoulder 73 of port 14 which is effected by contact with lip 71 of latch portion 69. Vial 11 is further sealed from diluent 82 with stopper 41 which has a small diameter section 47 and a larger diameter section 45. Each section has annular portions or rings 39 for sealable engagement with the inside of vial 11 such as with vial neck 49 and the vial finish section 53. Stopper 41 has a recess 61 with a flange 65. Recess 61 is designed to receive projection 59 having a lip 63 for engagement with flange 65 and a connecting portion 57 for cover 55. Cover 55 also includes a transverse wall 95 for interconnection with annular wall 67.

Figure 15:
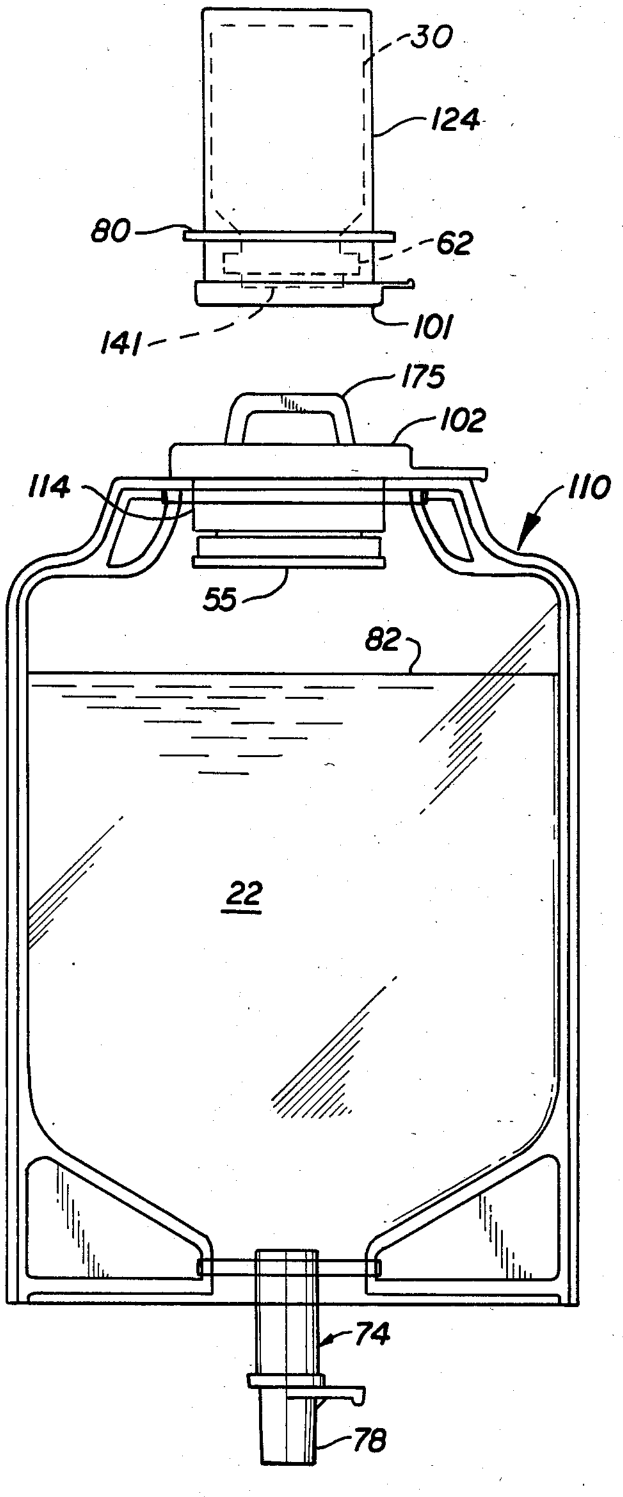
FIGS. 15 and 16 are views in side elevation showing the medicament vial before and after being secured to the flexible container.
Figure 16:
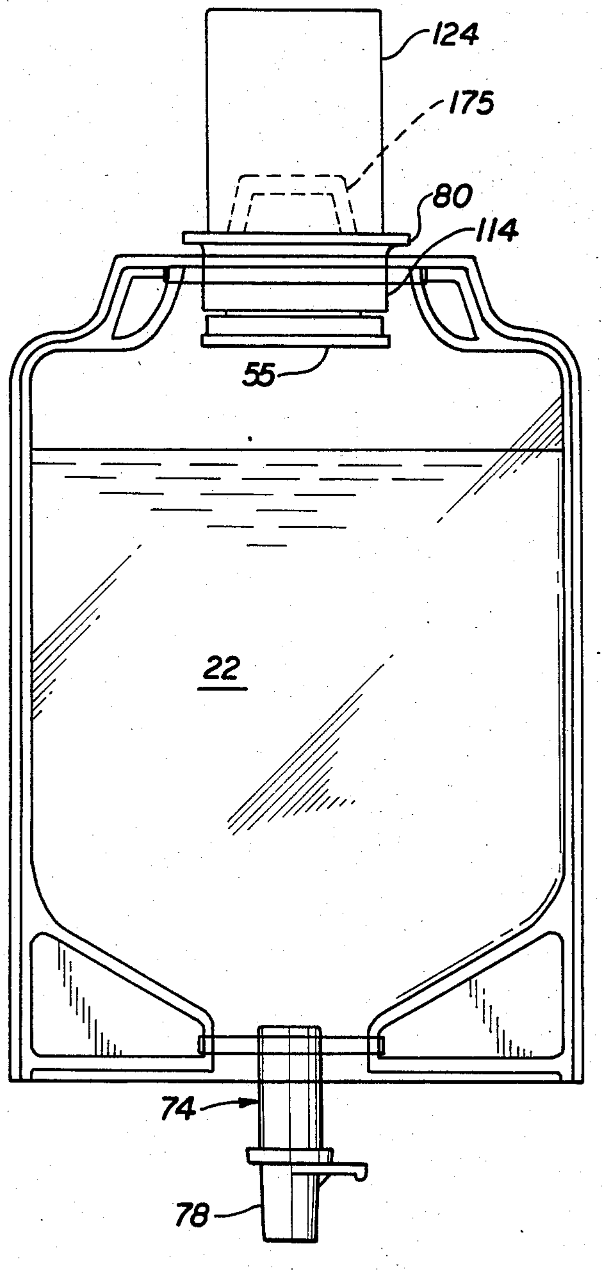
Figure 17:
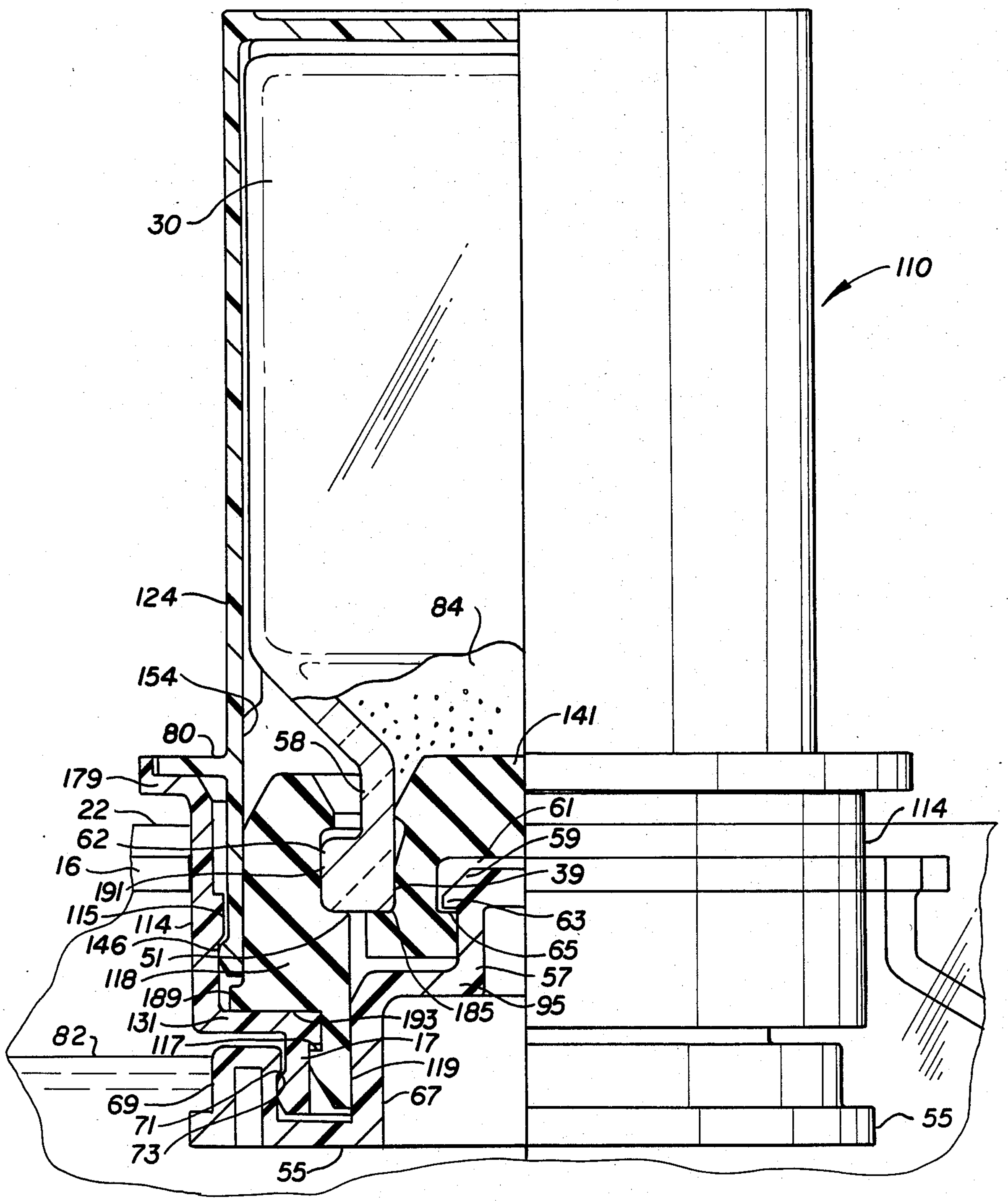
FIG. 17 is a view similar to FIG. 14 further illustrating the container system of FIGS. 15 and 16.

FIGS. 15, 16 and 17 illustrate another embodiment generally 110 wherein, as will be seen in FIG. 15, when the vial 30 is packaged separately from container 22, a sleeve 124 surrounds vial 30 except for the stopper portion 141. A cover cap 101 closes the sleeve which also includes flange 80. Similarly, a cover cap 102 will be positioned over port 114 from which also extends a hanger 175. Referring particularly to FIG. 17, port 114 has an internally extending flange 115 over which is positioned annular ridge 146 on sleeve 124. It should be pointed out that previously annular ridge 146 would have supported cover cap 101. In this position in port 114, sleeve flange 80 will contact port flange 179. A gasket 118 is positioned inside port 114 and includes a shoulder 193 for resting against shoulder 131 of port 114. A flange 117 extends from gasket 118 for sealable engagement with port 114. An annular recess 191 is provided in gasket 118 to receive rim 62 of vial 30 as well as to provide a seal with finish 51. Further sealing of the contents of vial 30 from diluent 82 is effected by stopper 141 with annular rings 39 which will seal the inside of vial neck 58. Additional fluid-tight sealing is afforded by a lip 185 extending from stopper 141 to also engage finish 51. Oppositely positioned is a flange 65 extending into compartment or recess 61 for contact with lip 63 extending from connecting portion 57. As the remaining portion of cover 55 with connecting portion 57 is the same as described in conjunction with embodiment 10, its description need not be repeated.

Figure 18:
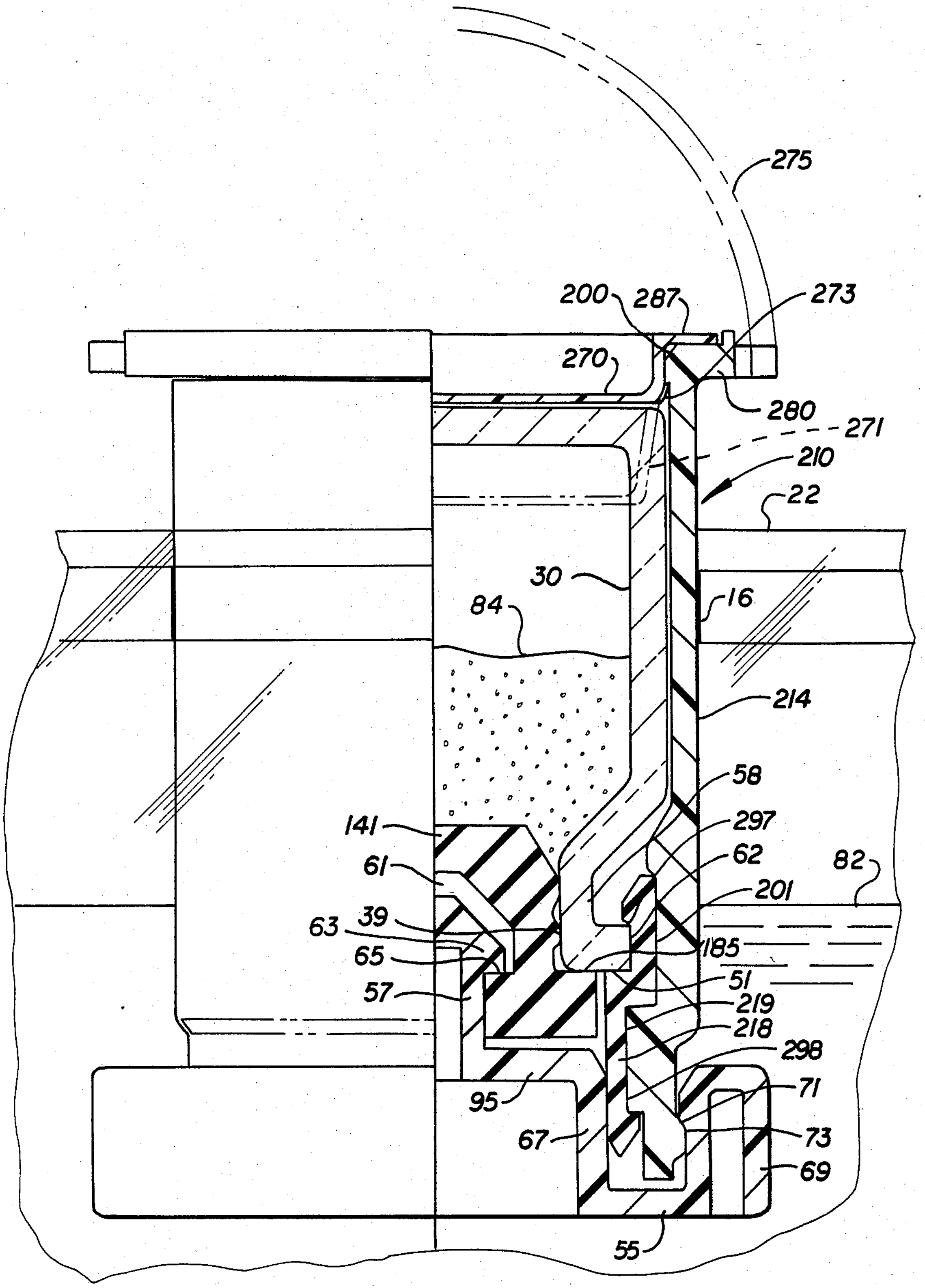
FIG. 18 is a view similar to FIG. 14 depicting still another embodiment of a medicament vial secured in a flexible container.

Referring to FIG. 18, an interconnection and sealing of the medicament 84 in vial 30 from diluent 82 in container 22 is different in this embodiment than in embodiments 10 and 110. In this embodiment 210, the rim 62 of vial 30 will be positioned and sealed in port 214 by means of recess 297 in gasket 218. Gasket 218 will be retained in port 214 by providing a recess 201 as well as a recess 298 in gasket 218 for reception of flange 219 extending from port 214. It will be seen that stopper 141 is substantially the same as previously described in embodiment 110 as well as the engagement with cover 55 and connecting portion 57 except that it includes a lip 185 for engagement with container lip 62. Accordingly, these same components and elements are referred to by the same numbers.

Figure 19:
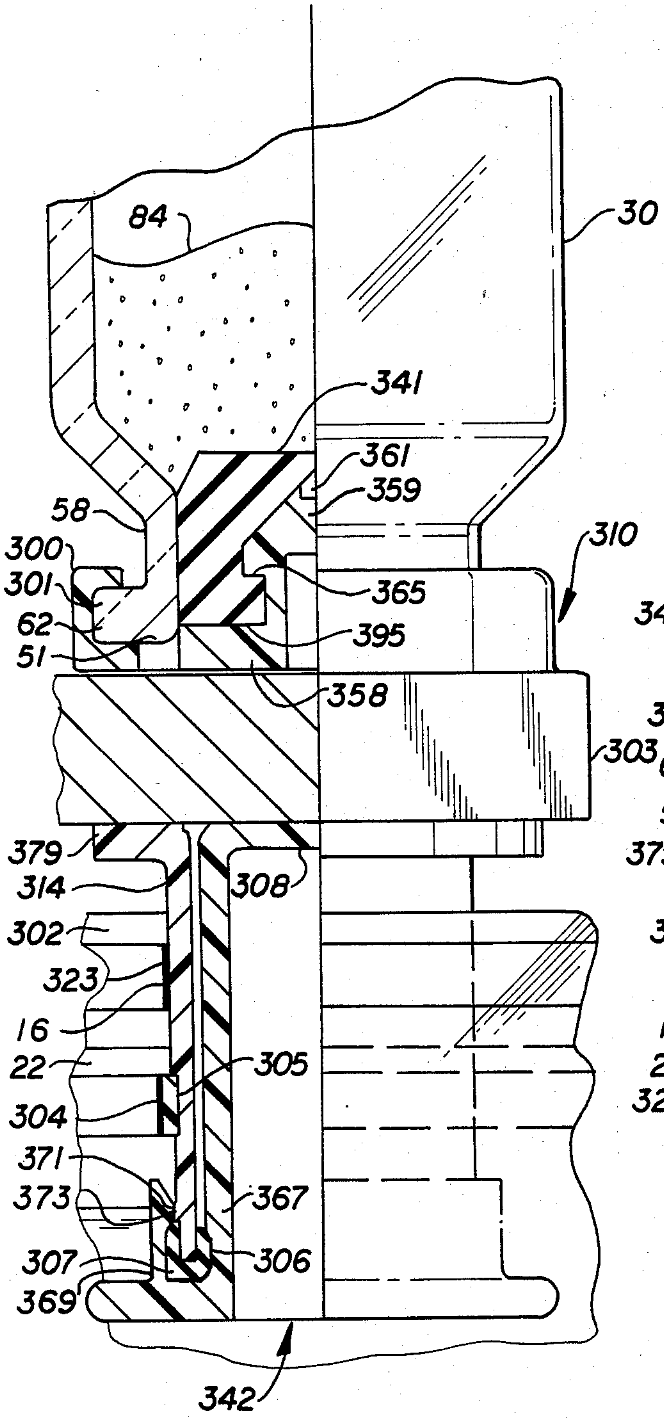
FIGS. 19 and 20 are views similar to FIG. 14 showing a method of securing a medicament vial to the port of a flexible container.
Figure 20:
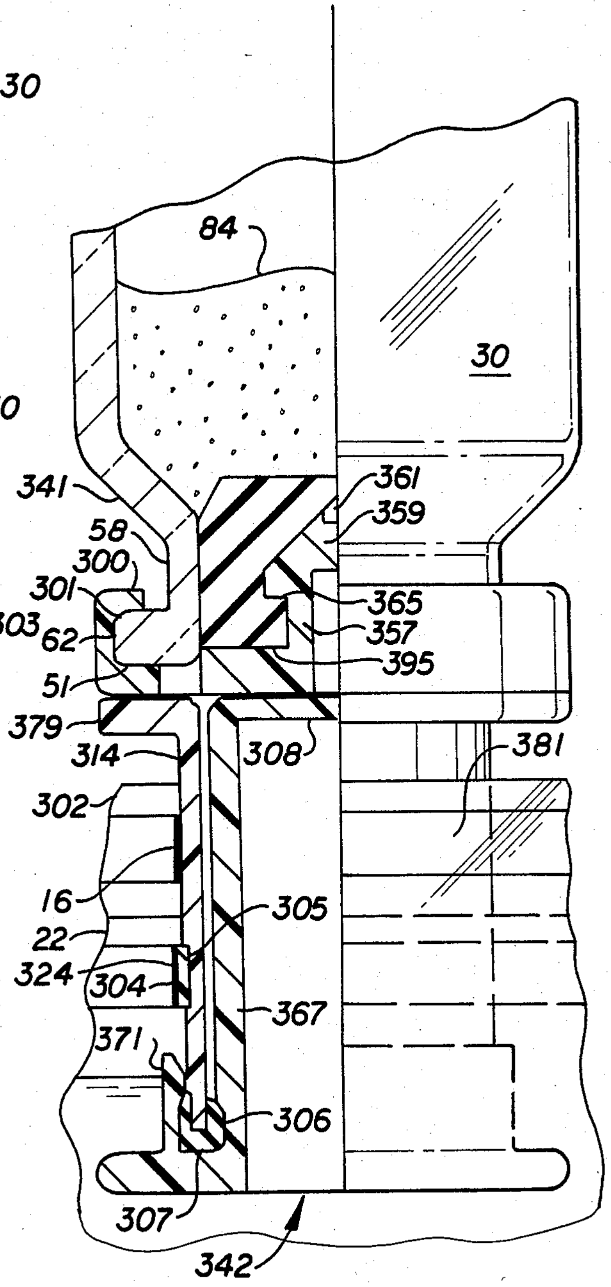
Figure 21:
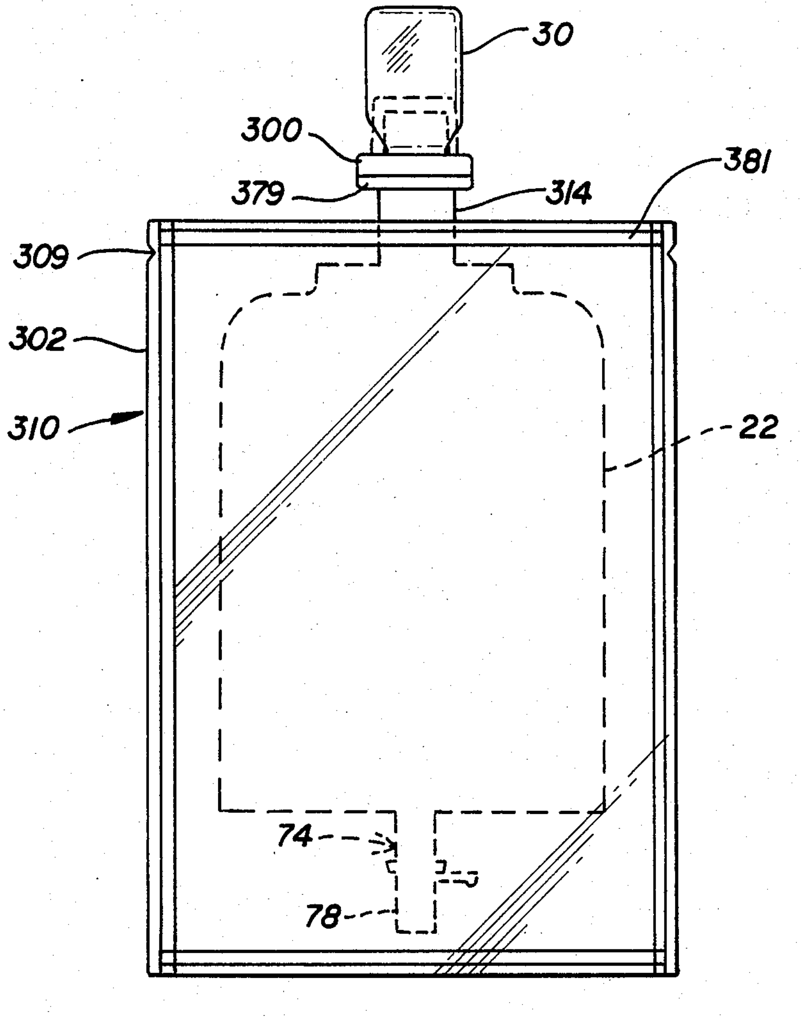
FIG. 21 is a view in side elevation illustrating the dual container shown in FIG. 20 as it would be packaged in an overwrap bag.
Figures 22A, 22B:
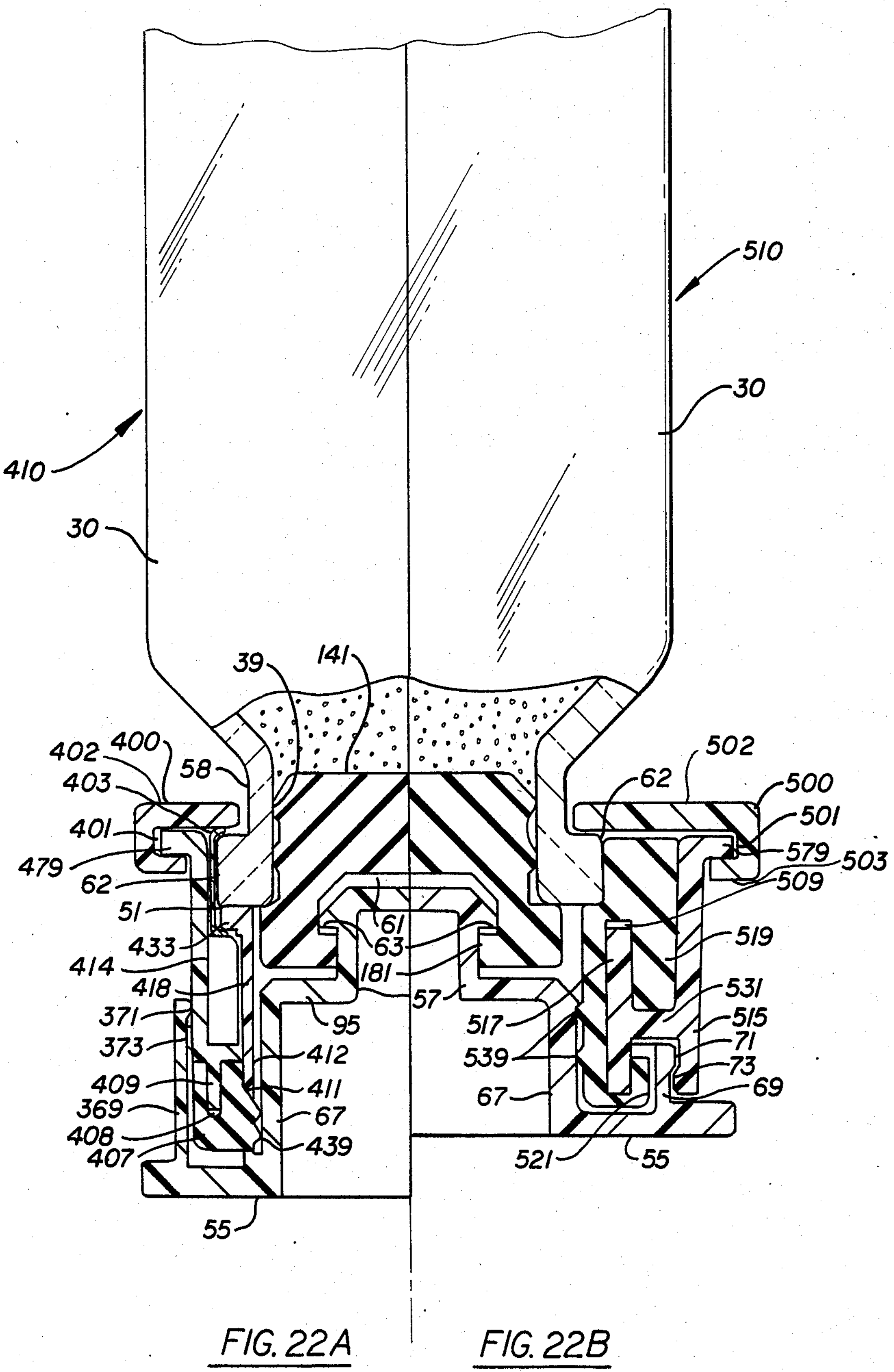
FIGS. 22A and 22B are views in side elevation and with a portion broken away illustrating two additional embodiments of medicament vials and container port attachment systems therefor.

Embodiment generally 310 in FIGS. 19, 20 and 21 depict vial unit 30 which when filled with medicament 84 can be directly heat sealed to port structure 314. In this embodiment, a stopper 341 closes neck 58 and has a compartment 361 for receiving projection 359 of connecting portion 357. A flange 365 extends from stopper 341 for engagement with projection 359 and has a transverse wall 395 for contact with a complementary wall section on stopper 341. Extending over container lip 62 is an annulus 300 having a recess 301 for partial fitment thereover. Container port 314 will have sealed thereto such as at 323 an overwrap 302 which will extend over flexible container 22. A gasket 304 will be accommodated in recesss 305 in port 314 for the purpose of making an adequate seal between container 22 and port 314. Gasket 304 is sealed at 324 to container 22 such as with R.F. welding but is friction sealed to port 314. A cover generally 342 has a compartment 306 with a gasket 307 to surround port 314. A latch portion 369 is provided on cover 342 for removable attachment to port 314 by means of lip 371 engaging shoulder 373 on port 314. Cover 342 also includes an annular wall 367 terminating in end wall 308 for sealing to insert 358 as will be later explained in the Operation. At the opposite end of port 314, a flange 379 extends laterally therefrom.

As seen in FIG. 21, overwrap 302 will be weld sealed at 381 and will surround port 314. The usual tear portion 309 is provided for removal of the overwrap.

Embodiments 410 and 510 which are illustrated in FIGS. 22A, 22B and 23–25 depict embodiments which utilize a latching collar such as 400 and 500 for securing container ports 414 and 515 respectively to container lip or rim 62. Referring specifically to embodiment 410, it will be seen that it includes a multi-component receiving and sealing system in that a ferrule 403 is positioned over finish 62 and will contact and retain shroud tube 418 against rim portion 62. Shroud tube 418 contacts finish 51 on container 30 and extends downwardly to seal against gasket 407 having recess 411 to receive extension 412 of shroud tube 418. Port 414 also includes a flange 409 for seating in slot 408 of gasket 407. Annular portions 439 extend from gasket 407 to seal against annular wall 67 of cover 55. Cover 55 with its associated connecting portion 57 for engagement with stopper 141 is the same as described in conjunction with embodiment 10 as indicated by the same reference numerals. This is also true with respect to the hereinafter described embodiment 510.

Embodiment 510 represents still another means of sealing a container vial 30 into a port structure 515. In this particular embodiment, port 515 has a leg portion 531 interconnecting with a T-shaped head portion 517. Positioned within this configuration is gasket 519 having a slot 509 to receive head portion 517 as well as an extension to partially surround a portion of head portion 517. Sealing rings 539 extend from gasket 519 to engage annular wall 67 of cover 55. Collar 500 has a recess 501 to surround flange 579 as well as to contact the upper portion of lip 62.

Figure 23:
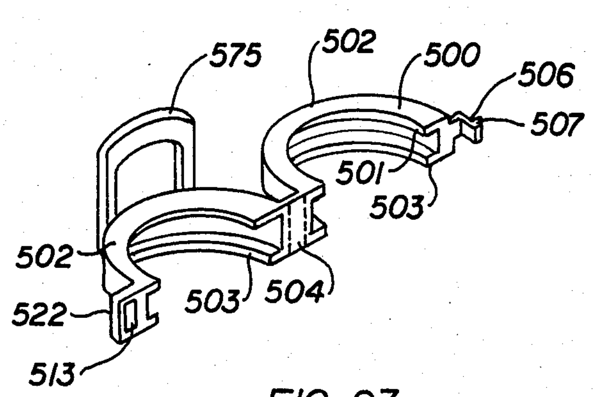
FIG. 23 is a perspective view of a latching collar member utilized in conjunction with the container systems shown in FIGS. 22A and 22B.
Figure 24:
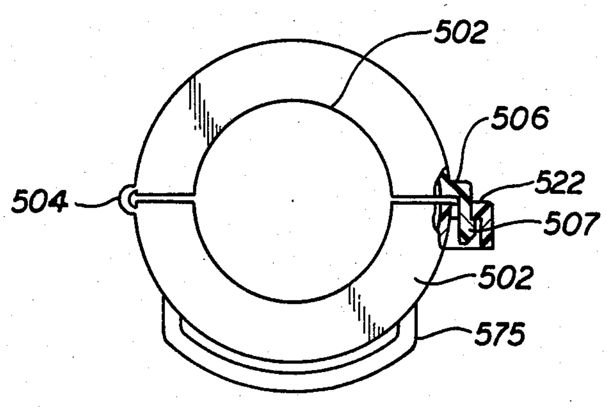
FIG. 24 is a top view of the latching collar shown in FIG. 23 in the closed position.
Figure 25:
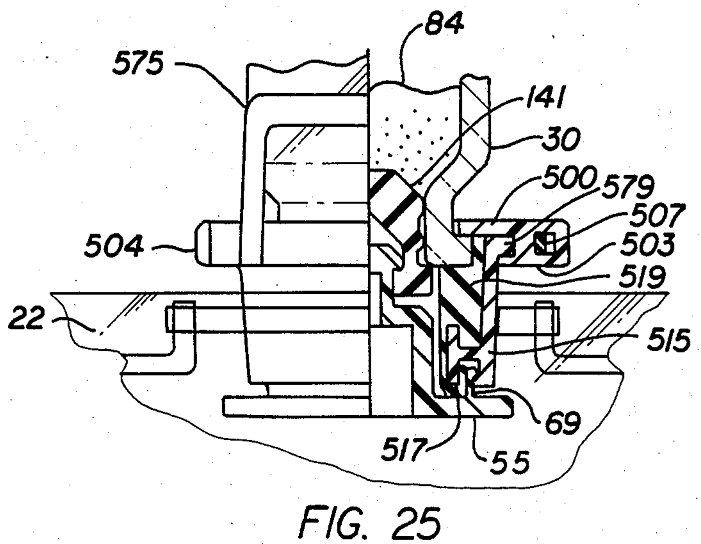
FIG. 25 is a view in partial side elevation and in partial vertical section depicting the locking of the collar shown in FIGS. 23 and 24 attached to the container system of FIG. 22B.

FIGS. 23–25 specifically show the collar 500 and its latching relationship with respect to vial 30. Collar 500 has a recess 501 surrounded by arcuate walls 502 and 503 which are connected by hinge portion 504. Extending from one end of the collar 500 is a latch member 506 with a barb portion 507 for placement through opening 513 and retention with wall 522 (see FIG. 24). A hanger portion 575 extends from collar 500 to support the interconnected vial 30 and container 22 as specifically shown in FIG. 25. It should be pointed out that collar 400 is of a similar construction to collar 500 and surrounds rim 62 of vial 410 and flange 479 in a similar manner as described for embodiment 510.

Operation

Figure 1B:
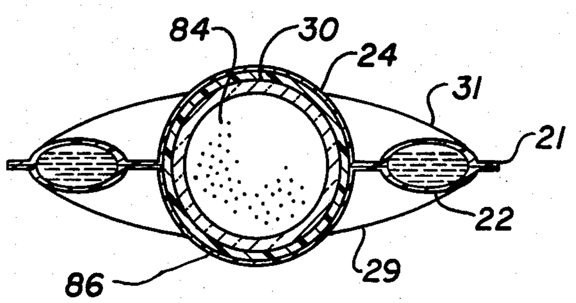
FIG. 1B is a view in horizontal section taken along line B—B of FIG. 1.
Figure 2:
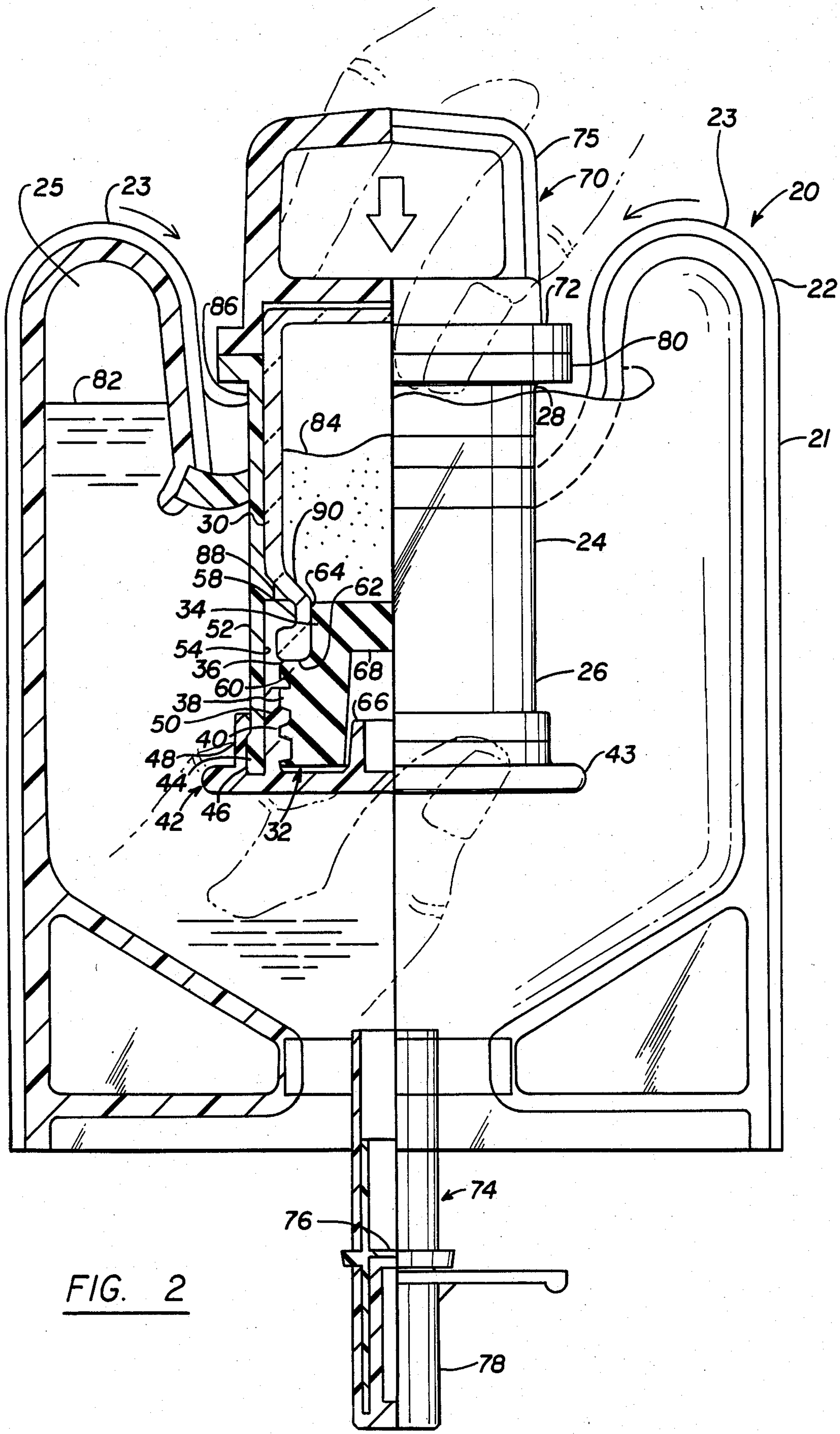
FIGS. 2, 3 and 4 are views similar to FIG. 1 showing the operation of the dual compartmented container illustrated in FIG. 1.
Figure 3:
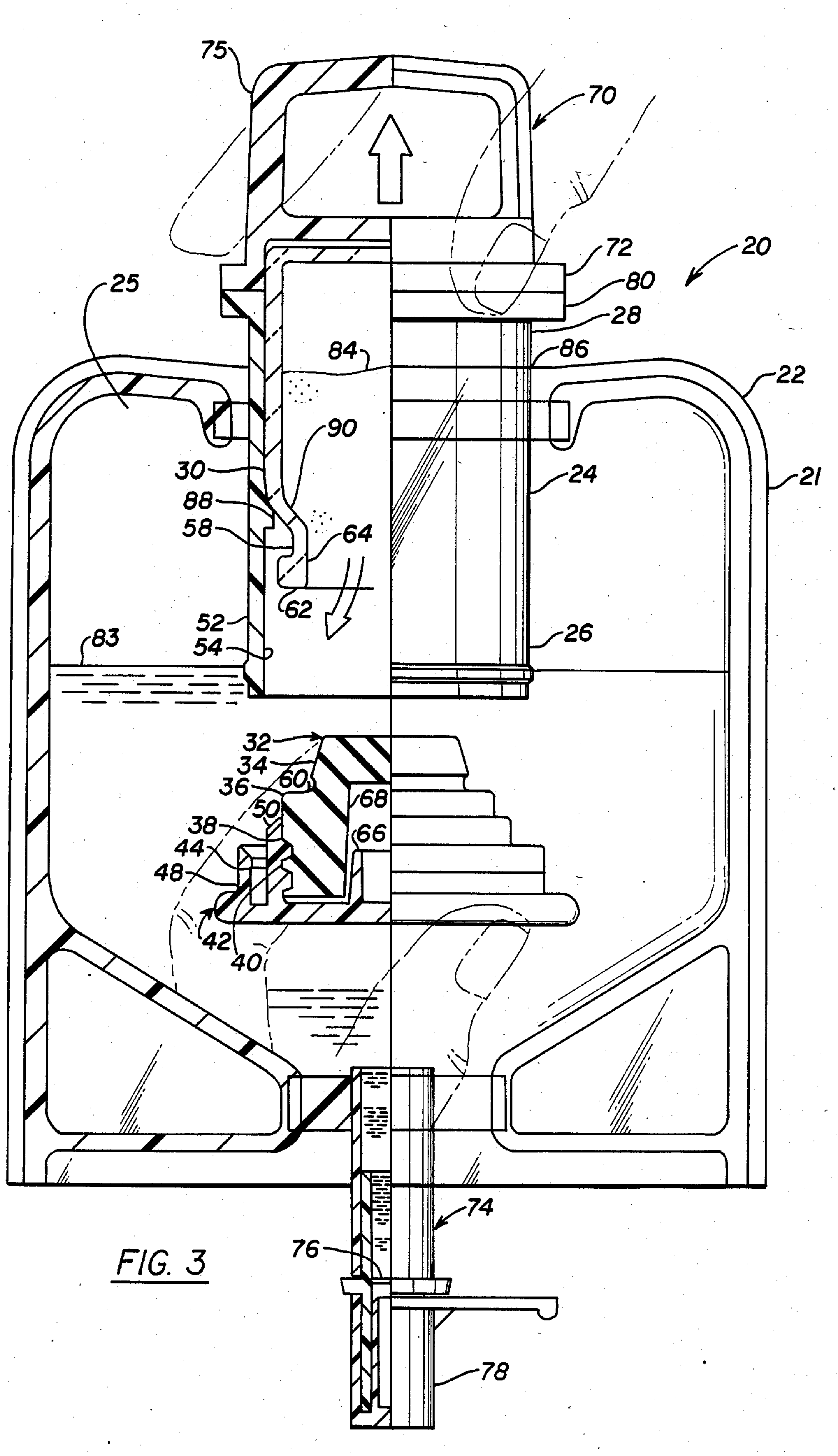
Figure 4:
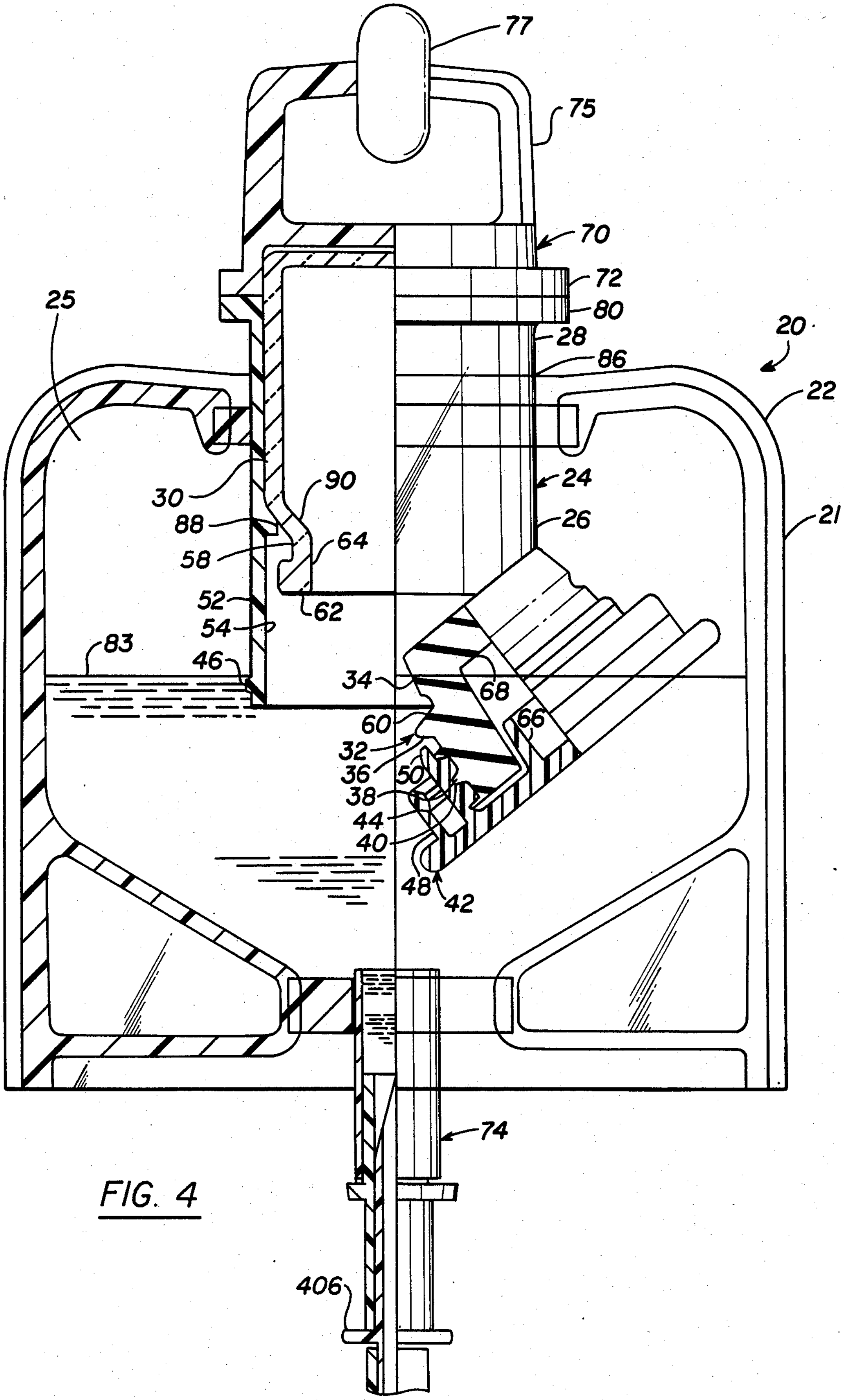

A better understanding of the advantages of the manually operated dual compartmented containers of this invention will be had by a description of their operation. The operation of the containers 20, 120, 220, 320, 420, 520, 620, 720, 820 and 920 will be described first. Dual compartmented container 20 generally will be received by health care personnel as shown in FIG. 1. Activation of the dual compartmented container 20 is begun as shown in FIG. 2. The cap 70 is grasped by the thumb and the forefinger, and used to push cover 42 into the central portion of flexible container 22. Although not essential to operability of the dual compartmented container 20 disclosed herein, forming the flexible bag 22 so that the top shoulders 23 are shaped in an arcuate manner and the longitudinal seams 21 on either side of sleeve 24 taper inward reduces the amount of manual force necessary to urge the sleeve 24 into the inner compartment 25 of flexible container 22. Once the cover 42 has been pushed into the central portion of the flexible container 22 the cover 42 is grasped from outside the flexible sides such as 29 of the container 22 as by pressing the adjacent portions of the walls 29 and 31 thereagainst (see FIG. 1B). Adding a flange 43 to the cover 42 facilitates this operation. By holding the cap 70 and manipulating cover 42 and stopper 32 combination from the outside the flexible container 22 the stopper 32 and cover 42 combination may be removed from the vial 30 as shown in FIG. 3. This will cause the medicament 84 to fall from within the vial 30 into the diluent 82 in compartment 25 of the flexible container 22. The exterior walls of the flexible container 22 may be further manipulated to assure complete mixing of the medicament 84 such as any one of a variety of powdered or liquid pharmaceutical products such as the following antibiotics: cephalothin, oxacillin, nafacillin, ampicillan, ticarcillin, carbenicillin, erythromycin, nitroprusside and succinylcholine, vitamin or nutritional preparations and a diluent 82 such as water or dextrose or saline solution to form mixture 83. Once mixed the visual indication of the stopper 32 and cover 42 combination in the mixture 83 as shown in FIG. 4 will indicate that the dual compartmented container has been activated. Hanger 75 may be used to attach the dual compartmented container 20 to a hook from an I.V. pole 77.

The embodiments shown in FIGS. 5–7 and 9–13 are operated in a similar manner to that described in FIGS. 1–4 except as more specifically described below.

Referring specifically to the embodiment shown in FIGS. 5 and 5A toggle means 188 is contacted by pressing the walls 29 and 31 of flexible container 22 thereagainst. Toggle means 188 is pressed inward to effect fluid communication between the two compartments. The straightening action of toggle means 188 causes the stopper 32 and cover 42 combination to be removed from the neck 58 of vial 30 thus allowing medicament 84 to pass into diluent 82 as shown in FIG. 5A.

In the FIG. 6 embodiment the stopper 32 and cover 42 combination do not fall into mixture 83. Rather, they are retained on sleeve 24 by strap 296.

The FIG. 7 embodiment operates in a manner similar to that of FIG. 1 except that instead of manipulating the stopper 32 and cover 342 combination through the walls 29 and 31 of flexible container 22, tab means 398 are grabbed from only one flexible side of container 22 to assist in removing the stopper 32 and cover 342 combination.

In the FIG. 8 embodiment 420, the dual compartmented container is shown without a diluent in container 22. In this condition, diluent may be added through a syringe cannula 404 or spike 406 inserted in port 74. Once the diluent has been added to container 22, the dual compartmented container activated and the medicament mixed with the diluent, spike 406 may be attached to an I.V. administration set. Alternatively a second port 402 may be used for the addition of an additive material into container 22 in the usual manner.

In the FIG. 9 embodiment 520, flanged tapered ring 510 is moved outwardly with respect to outwardly tapering portion 516 of sleeve 524. This outward movement releases the pressure on outwardly tapering portion 516 and thus reduces the force on protrusion 540 which holds cover 542 onto sleeve 524. Flanged tapered ring 518 may be moved upward and outward on sleeve 524 until strap 596 is fully extended. The engagement of projection 512 from cover 542 on the underside of lip 511 on stopper 532 causes stopper 532 to leave the vial 530 when downward force is exerted on cover 542. The medicament 84 is then combined with diluent 82 in container 22.

Referring to the embodiments shown in FIGS. 10 and 11, they have extended portions 610 and 710 respectively, effecting a better seal connection and not affecting operability.

The embodiment shown in FIG. 12 offers the advantage of tab means 898 being grabbed through one of the flexible sides such as 29 of container 22 to separate the weak weld 850 which joins cover 842 to flange 846 and removes stopper 32 from vial 30.

The embodiment 920 shown in FIG. 13 operates exactly the same as in FIG. 1.

The operation of the embodiments shown in FIGS. 14–25 will now be described.

As indicated earlier, vials 11 and 30 will be supplied independently of the flexible container 22 and will be packaged in a manner indicated in FIG. 15. Vial 30 in this instance will include stopper 141 covered by cover cap 101. When it is desired to mix the contents of vial 30 into solution container 22, the caps 101 and 102 will be removed and the adjacent portion of sleeve 124 will be inserted into port 113 with annular ridge 146 riding over flange 115 in port 114 (see FIG. 17). At the same time, vial rim 62 will sealably engage annular recess 191 of gasket 118.

Simultaneously, lip 63 of connecting portion 57 will be seated in recess 61 and adjacent flange 65. Further sealing is afforded by gasket 118 with extension 119 sealing against wall 67 of cover 55. If desired, sealing rings such as 39 could be provided on extension 119 for contact with wall 67. It will be appreciated that cover 55 as well as gasket 118 will previously be positioned in port 114 with cover 55 placed within the confines of container 22. Embodiment 110 will be activated in the manner previously described for embodiments numbered in the "20" series. This is effected by pushing vial 30 further into the body of container 22 as indicated in FIG. 2, which positioning is accomplished by the flexing of shoulders 23. When vial 30 assumes a position as indicated in FIG. 2, cover 55 will be grasped, preferably by the thumb and forefinger, and facilitated by flange 179. A pulling action away from vial 30 will cause latch portion 69 to disengage shoulder 73. This in turn will effect a pulling action on stopper 141 which force will be transmitted through connecting portion 57 to projecting lip 63 acting on stopper flange 65. A continuous pulling action will then cause stopper 141 to be removed from neck 58 of vial 30 to thereby permit medicament 84 to flow into diluent 82. Accordingly, cover 55 with connection portion 57 and projecting lip 63 affords a stopper removal means.

It will be appreciated that embodiment 110 offers a tamper indicating system in that once the vial 30 is placed in port 114 and lip 63 enters recess 61, any attempt to remove vial 30 will effect a removal of stopper 141 and a spillage of powder 84 which is readily observed. Embodiment 110 also offers the versatility of being preassembled. This could be effected by sealing sleeve flange 80 to port flange 179.

The interconnection of vial 11 into port 14 in embodiment 10 will be substantially the same as previously described for embodiment 110, the difference being that instead of a flange-type fitment of a sleeve and container finish into a port, there is instead a screw-thread action provided by the interthreading of screw threads 13 and 15. The screw action will continue until via finish 51 will come to rest on gasket 18. At the same time, projection 59 will be positioned in recess 61 so that stopper 41 can be removed in the manner previously described in connection with embodiment 110 by removal of cover 55 from port 14.

Referring to embodiment 210, a major distinction in its operation is in the securing of vial 30 inside port 214. There it will be seen that vial 30 will be placed with its associated stopper 141 into port 214 by seating vial rim 62 in recess 297 of gasket 218. With the vial properly seated, retainer plug 270 will be placed over the end of container 30 to secure it therein. It will be noted that retainer plug 270 includes a shoulder portion 200 for engagement over a portion of flange 280, which shoulder is in effect formed in part by flange 287. Retainer plug will also be aided in its engagement with port 214 by means of undercut 273 engaging port 214. In the instance where a shorter vial is employed, a larger or deeper plug 271 can be employed which will be retained in port 214 in the same manner as described for plug 270. As in the previous embodiments, with the placement of vial 30 in port 214, connecting portion 57 with lip 63 will engage flange 65 of stopper 141. Activation of this particular container system 210 will be as indicated in the previous embodiments 110 and 10.

Referring to embodiment 310, it is different from the previous ones in that container 30 will be integrally connected to port 314 and will be done so at the time of fabrication. This will be effected by the use of hot plate or bar 303 which will, as indicated in FIG. 19, contact adjacent portions of annulus 300 and flange 379 as well as end wall 308 with insert 358. When in a heated state, the heated thermoplastic surfaces will then be pressed together to result in a container system as depicted in FIG. 20. This heating procedure offers the advantage of presenting sterile adjacent surfaces of flange 379 to annulus 300 and adjacent surfaces of end wall 308 to insert 358. To activate this container system, cover 342 will be unlatched from port 314 by removal of lip 371 from port 314 which will effect a pulling action and removal of stopper 341 due to the fusion of end wall 308 with transverse wall 395 forming a connecting portion 357.

The operation of embodiments 410 and 510 are different from those previously described in the use of latching collars 400 and 500, which will maintain container 30 in connection with respective ports 414 and 515 once the vial is placed into the port with rim 62 placed in seating engagement with shroud tube 418 and gaskets 519, respectively. As will be seen in FIGS. 22A, 22B and 25, collars 400 and 500 will capture flanges 479 and 579 respectively, in a recess such as 501 with upper arcuate walls 402 and 502 contacting ferrule 403 on lip 62 in embodiment 410 or directly on lip 62 in the instance of embodiment 510. After the latching action of the respective collars 400 and 500, the activation of both of these container systems 410 and 510 will be as previously described with the removal of covers 55 and the pulling action effected on stopper 141 by means of connecting portion 57.

While several means exist for manufacture and assembly of the dual compartmented container it is preferable to begin by forming the flexible container from two sheets of flexible material in order to form side walls 29 and 31. An opening 86 is left at the top of the container for sleeve 24 or ports 14, 114, 414 and 515, and at the bottom of the container for port 74. Covers 42, 55, 342, sleeve 24 and the ports are assembled under sterile conditions and RF mandrel sealed or heat sealed through the edge of the flexible container 22. Similarly, port 74 is RF sealed or heat sealed into the flexible container 22. The flexible container 22 may then be sterile filled with diluent 82 through port 74. Once filled the 'H' shaped administration port 76 and cap 78 are placed on port 74. Vial 30 is filled with medicament 84 and sealed by stopper 32 under sterile conditions. In the instance of the embodiments shown in FIGS. 1–13, once assembled, the filled and stoppered vial 30 is inserted under sterile conditions through sleeve 24 so as to operably engage stopper 32 with cover 42. Cap 70 may now be attached to sleeve 24 by RF weld or heat sealing flange 80 to flange 72. In the instance of the embodiments illustrated in FIGS. 14–22B, after the vials 30 or 11 are filled and stoppered, they will be covered with a closure cap such as 101 as will the container port such as 114 with closure cap 102.

The embodiment shown in FIG. 13 provides an alternate means of manufacture. Instead of inserting vial 30 from the top of sleeve 24 as in the other embodiments, the sealing of vial receiving casing 923 into the edge 21 of flexible container 22 permits the pre-filled, sterilized and capped vial to be inserted through the flexible container 22 into vial receiving casing 923. Cover 42 is placed on stopper 32 before insertion of vial 30 through flexible container 22 into vial receiving casing 923. Vial 30 is held in place by the snap-fit of lip 44 on cover 42 over ridge 946 on vial receiving casing 923 in a manner similar to that shown in FIG. 1.

It will be appreciated that in embodiments 10, 110, 210, 310, 410 and 510, interconnection between vial containers 11 and 30 and the flexible container 22 is afforded by container port engagement means provided by the flexible container ports and complementary engagement means provided by the container vials 11 and 20. The engagement means provided by the container ports is represented by threads 15 in embodiment 10; flange 115 in embodiment 110, recess 297 in gasket 218 in embodiment 210; flange 379 in embodiment 310; gasket 407 in embodiment 410 and gasket 519 in embodiment 510. The respective complementary engagement means of vial containers 11 and 30 is represented by threads 13 in embodiment 10; flange 146 in embodiment 110; annulus 300 in embodiment 310; shroud tube 418 in embodiment 410 and vial rim 62 in embodiment 510.

The preferred material for manufacturing the flexible container cap 70, sleeve 24 and the port receiving vials is a translucent polyester or a polypropylene plastic material. However, other resinous materials such as a polyvinyl chloride or polyethylene may be used. The preferred material for covers 42, 55 and 342 is polyethylene; however, polyester or polypropylene may be used. Stoppers such as 32, 41, 141, 341 as well as gaskets such as 18, 118, 218, 418, 519 as well as 407 and 307 are fabricated from rubber, however a flexible plastic may be used such as thermoplastic resin. Vials 11 and 30 are preferably made of glass, however a rigid or semi-rigid plastic such as polypropylene or polycarbonate may be substituted for glass.

While the present dual compartmented container has been preferably described for use with a powdered medicament in a vial and a liquid in the bag, it is obvious that the container is usable with any fluid material. For example, a liquid could be placed in the vial for mixing with liquid in the bag. Further, while the present dual compartment container has been described for use with fluid materials in the health care field, it will be appreciated that the dual compartmented container system can be applied to other fields. For example, it would have application with any fluid materials where it is necessary to maintain two materials in a separate condition until prior to mixing and use, and where one of the materials to be maintained is sensitive to ambient conditions. It should be understood that the term "fluid material" or "fluid contents" as employed in the specification or claims is meant to imply any medicament or diluent material which will flow from one container to another whether a liquid, solid or gas.

It will thus be seen that through the present invention there is now provided a manually operable dual compartmented container which is easily manufactured and used. The container system of this invention affords a sterile environment for fluid materials of any type during storage as well as mixing, yet in a manner that provides an inexpensive system. A unique sealing arrangement is also afforded between two containers which will provide a proper moisture barrier and substantially reduce the transmission of one material into the other until intentional mixing is desired.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An additive container for storing a sterile fluid and for mixing such stored fluid with the fluid contents of a flexible container having wall means which is deformable inwardly for manipulation of a stopper removal means therein and which has a port with additive container engagement means, and stopper engagement means in the flexible container for removing a stopper from an additive container engaged by said additive container engagement means, said additive container comprising:

a container having a removable stopper;

said container including complementary engagement means for interconnection with said additive container engagement means; and said stopper including means for connection with such a stopper engagement means in such a flexible container when said complementary engagement means is interconnected with the additive container engagement means of the flexible container;

whereby when said complementary engagement means is interconnected to said additive container engagement means of said flexible container and connection means of said stopper interconnects with said stopper engagement means of said flexible container and exterior manipulation from outside said flexible container of said stopper engagement means will effect removal of said stopper from said container allowing the fluid contents of the containers to intermix in said flexible container.

2. The device as defined in claim 1, wherein said complementary engagement means is defined by external threads extending from a neck portion of said additive container for engagement with internal threads of such a port; and said connection means of said stopper is defined by a recess in said stopper for engaging a connecting portion of such a stopper engagement means in said recess.

3. The device as defined in claim 1 wherein said complementary engagement means is defined by a sleeve member having a ridge member extending therefrom for engagement with a flange extending from said port; and said stopper engagement means is defined by a recess in said stopper for engaging a connecting portion of such a stopper engagement means in said recess.

4. The device as defined in claim 1 wherein said container includes at least one annular surface disposed for abutting engagement with sealing means of such a flexible container when said container with said stopper is interconnected therewith, said complementary engagement means being of a configuration for interconnection with such additive container engagement means by relative rotation between said container and said flexible container and thereby also effecting axial movement of said container relative to such a flexible container for sealing abutment of said annular surface with such sealing means and interconnecting said stopper connection means with such stopper engagement means of the flexible container.

5. The device as in claim 4 wherein said complementary engagement means is defined by external thread elements on said container for engagement with internal thread elements of such a port.

6. A fluid container for holding a fluid and receiving a medicament thereinto from an independent medicament container having an egress opening closed by a sealing barrier, said fluid container constructed to define a sealed compartment for storing a sterile liquid, said fluid container having flexible walls, a portion of said fluid container defining an inlet passageway to said compartment through said walls and including means for affixing such an independent medicament container to said fluid container with the opening of such medicament container in communication with said passageway and with said sealing barrier of said medicament container exposed to said passageway, and means within said compartment and manipulatable through said flexible walls for removing said sealing barrier from a medicament container so affixed by said affixing means to open such an affixed medicament container, said flexible walls being of a material and construction such that said walls are deformable inwardly for manipulation of said removing means through said walls for so removing said sealing barrier, whereby a medicament will flow from such an affixed medicament container into said first compartment through said passageway.

7. A device for separately storing and subsequently mixing the fluid contents of two containers wherein a removable barrier separates the containers, said device comprising:

a first flexible container constructed to enclose a first compartment, said container having flexible wall means and at least one port;

a second container constructed to enclose a second compartment, said second container having a throat and a removable stopper disposed at least partially within said throat, said second container being secured to said first flexible container through said wall means of said first flexible container with said throat and stopper disposed inwardly relative to said compartment;

stopper removal means with a portion thereof operatively positioned within said first compartment and connected to said removable stopper for removing said stopper;

said flexible wall means being of a material and construction such that the wall means is deformable inwardly for manipulation of said stopper removal means through said wall means;

said stopper constructed and arranged to be removable from said second container by such manipulation of said stopper removal means from outside said flexible container wall means;

whereby through exterior manipulation from outside said wall means of said flexible container the stopper of said second container may be removed from said second container allowing the fluid contents of the containers to intermix through the throat of said second container.

8. The device as defined in claim 7 wherein said first container includes wall means with an edge portion and said second container is fixedly disposed through said edge portion.

9. The device as defined in claim 8 wherein said edge portion of said first container is defined by two separate shoulder sections and includes arcuate portions and inwardly tapering longitudinal seams on either side of said second container.

10. The device as defined in claim 7 wherein said flexible container includes wall means with an edge portion; container receiving means for said second container positioned through said edge portion and said second container has complementary receiving means for engagement with said second container receiving means.

11. The device as defined in claim 10 wherein said first container includes a port member with said stopper removal means positioned therewith.

12. The device as defined in claim 11 wherein said second container receiving means and said complementary receiving means are defined by screw threads.

13. The device as defined in claim 11 wherein said second container receiving means and said complementary receiving means are definėd by engageable flanges extending from said second container and said flexible container.

14. The device as defined in claim 7 wherein said first container includes a plurality of ports.

15. The device as defined in claim 7 wherein the second container is made of glass.

16. The device as defined in claim 7 wherein said stopper is made of rubber.

17. The device as defined in claim 7 wherein said second container contains a powdered or liquid medicament and the first flexible container contains a diluent.

18. The device as defined in claim 7 wherein said first container includes rounded shoulder portions adjacent said second container said shoulder portions constructed and arranged to permit movement of said second container inwardly of said first container.

19. The device as defined in claim 7 wherein said port is adapted to receive an administration spike of an I.V. administration set.

20. The device as defined in claim 7 including a member disposed through said wall means and defining an inlet to said compartment of said flexible container, said second container being secured to said member with said throat and stopper aligned with said inlet.

21. The device as defined in claim 20 wherein said second container has an outlet portion around said throat, and said member including means for engaging said second container and effecting sealing engagement of said outlet portion with said member around said inlet.

22. The device as defined in claim 20 including a removable element sealing said inlet; said removable element, said stopper and said removal means being joined together whereby such manipulation of said removal means removes said removable element and said stopper.

23. A dual compartmented container having a means for intermixing fluid contents of the compartments, said container comprising:

a flexible outer container constructed to enclose a first compartment, said outer container having an edge and opposing sides;

a member disposed through said edge of said flexible outer container and defining an inlet to said compartment therein;

a vial enclosing a second compartment and having a throat and a removable stopper at least partially disposed within the throat of said vial, said vial positioned with at least the throat and stopper portion thereof within said member and with said throat and stopper aligned with said inlet to said flexible container;

means disposed within said first compartment for removing said stopper by manipulation through said sides of said flexible outer container;

said flexible outer container being of a material and construction such that said sides thereof are deformable inwardly for manipulation of said means for removing said stopper;

whereby through exterior manipulation from the side or sides of the flexible outer container the stopper may be removed from the vial allowing the fluid contents of said vial and said flexible outer container to intermix through the throat of said vial.

24. The dual compartmented container as defined in claim 23 wherein said member includes a hanger means.

25. The dual compartmented container as defined in claim 23 wherein said vial defines an angled wall portion and said member defines an annular ridge contacting the angled wall portion of said vial.

26. The dual compartmented container as defined in claim 23 wherein said means includes a cover engaging said member and said stopper;

said cover constructed and arranged to be removable from said member by manipulation through said sides of said flexible container while maintaining engagement with said stopper;

whereby through exterior manipulation of the cover from the side or sides of the flexible outer container the stopper may be removed from the vial allowing the contents of said vial and said flexible outer container to intermix.

27. The dual compartmented container as defined in claim 26 wherein said member and said cover are made of plastic.

28. The dual compartmented container as defined in claim 26 wherein said cover includes a flange for removal of said stopper.

29. The dual compartmented container as defined in claim 26 wherein said cover includes a tab for removal of said stopper.

30. The dual compartmented container as defined in claim 26 further including strap means connecting the said cover and said member.

31. The dual compartmented container as defined in claim 26 further including toggle means connecting said cover and said member.

32. The dual compartmented container as defined in claim 26 wherein said cover includes a ring means and strap means connecting the cover and said member.

33. The dual compartmented container as defined in claim 26 wherein said cover and said stopper are operatively engaged by rotatable engagement means and said dual compartmented container includes latch means connecting said cover and said member.

34. The dual compartmented container as defined in claim 26 wherein said cover includes tab means, said cover and said stopper are interconnected by rotatable engagement means and said dual compartmented container includes flanges connecting said cover and said member, said flanges being separable by exterior manipulation of said tab means.

35. The dual compartmented container as defined in claim 26 further including latch means connecting said cover and said stopper;

said cover including tab means and said cover and said member defining flanges for interconnection therebetween;

said flanges being separable by exterior manipulation of said tab means.

36. The dual compartmented container as defined in claim 26 further including first latch means connecting said cover and said stopper and second latch means connecting said cover to said member.

37. The dual compartmented container as defined in claim 26 wherein said cover engages said vial as well as said member and said stopper.

38. The dual compartmented container as defined in claim 37 wherein said cover and said vial are engaged by rotatable engagement means.

39. The dual compartmented container as defined in claim 37 wherein said cover and said vial are engaged by latch means.

40. The device as defined in claim 23 wherein said vial has an outlet portion around said throat, and said member including means for engaging said vial and effecting sealing engagement of said outlet portion with said member around said inlet.

41. The device as in claim 23 wherein said first flexible container is formed of two sheets of flexible material sealed to one another at their edges and having respective edge portions sealed to said member to form a sealed connection therewith.

42. A device for separately storing and subsequently mixing the fluid contents of two containers in one of the containers wherein a removable barrier separates the containers, said device comprising:

a first flexible outer container constructed to enclose a fluid and having an edge, opposing sides and at least one port;

a second container enclosing a fluid material therein and having a throat and a stopper at least partially disposed within said throat, said second container fixedly disposed through the edge of said first flexible outer container, with said stopper of said second container positioned in said first container;

means disposed within said flexible outer container for removing said stopper from said second container by manipulation of said means through said sides of said container;

said flexible outer container being of a material and construction such that said sides thereof are deformable inwardly for manipulation of said means for removing said stopper;

whereby a fluid material may be introduced into said first flexible container by means of said port, and through exterior manipulation from the side or sides of the first flexible outer container the stopper may be removed from the second container allowing the fluid contents of the containers to intermix through the throat of said second container.

43. The device as defined in claim 42 wherein said port is constructed and arranged to initially receive a filling cannula or spike and subsequently a cannula or spike of an I.V. administration set.

44. The device as defined in claim 42 wherein said outer container contains two ports, one for filling and one for administration.

45. The device as defined in claim 42 wherein said second container contains a powdered or liquid medicament and said first flexible container is adapted to receive a diluent.

46. A device for separately storing and subsequently mixing the fluid contents of at least two containers wherein a removable stopper separates the containers, said device comprising:

a first container constructed to enclose a first compartment, said first container having flexible wall means and at least two ports;

a second container constructed to enclose a second compartment, said second container having a removable stopper;

one of said ports defining means for engaging such a second container and means for engaging such a stopper; at least a portion of said stopper engaging means being disposed in said first compartment for manipulation through said flexible wall means;

said flexible wall means being of a material and construction such that the wall means is deformable inwardly for such manipulation of said stopper engaging means through said wall means;

said second container including first complementary engagement means for interconnection with said second container engaging means, and said stopper including second complementary engagement means for interconnection with said stopper engaging means when said first complementary engagement means is interconnected to said second container engaging means, for removing said stopper;

whereby subsequent exterior manipulation of said stopper engaging means from outside said flexible wall means will effect removal of said stopper from said second container allowing the fluid contents of the containers to intermix in said first container.

47. The device as defined in claim 46 wherein said container engagement means and first complementary engagement means are defined by internal threads extending from said port and external threads extending from a neck portion of said second container; and said stopper engagement means and said second complementary engagement means are defined by a recess in said stopper and a connecting portion for engagement in said recess.

48. The device as defined in claim 47 further including a gasket member positioned in said port for contact with the finish of said second container.

49. The device as defined in claim 46 wherein said container engagement means and first complementary engagement means are defined by a sleeve member having a ridge member extending therefrom and a flange extending from said port for engagement therewith; and said stopper engagement means and said second complementary engagement means are defined by a recess in said stopper and a connecting portion for engagement in said recess.

50. The device as defined in claim 49 further including a gasket member positioned in said port for contact with the finish and a rim portion of said second container.

51. The device as defined in claim 46 wherein said second container engagement means and first complementary engagement means are defined by an annular member extending laterally from the neck of said second container and a gasket member with a recess for engagement with said annular member; and said stopper engagement means and said second complementary engagement means are defined by a recess in said stopper and a connecting portion for engagement in said recess.

52. The device as defined in claim 51 further including a gasket member positioned in said port for contact with the finish of said second container.

53. The device as defined in claim 51 further including a gasket member positioned in said port for contact with the finish and a rim portion of said second container.

54. The device as defined in claim 46 wherein said second container engagement means and first complementary engagement means are defined by a flange member extending outwardly from said port, an annular member extending laterally from the neck of said second container and a collar member for engagement with said flange member and said annular member; and said stopper engagement means and said second complementary engagement means are defined by a recess in said stopper and a connecting portion for engagement in said recess.

55. The device as defined in claim 46, wherein said second container engagement means and first complementary engagement means are defined by a lip member extending laterally from the neck of the second container, a flange member extending laterally from said port, an annular member with a recess for accommodating a portion of said lip member and said flange member; and said stopper engagement means and said second complementary engagement means are defined by a recess in said stopper and a connecting portion for engagement in said recess.

56. The device as defined in claim 55 wherein said second container engagement means and first complementary engagement means are further defined by a tubular shroud member secured to said lip member of said second container by a ferrule member, and a gasket member secured to said port for engagement with said shroud member.

57. The device as defined in claim 46 wherein said second container engagement means and first complementary engagement means are defined by a rim portion of said second container, an annular member of thermoplastic material positioned over at least a portion of said rim portion, a thermoplastic port with a portion of said stopper engagement means positioned therein and also formed from a thermoplastic material, said annular member and a portion of said port being sealed to each other, and said second complementary engagement means including a thermoplastic element connected to said stopper and sealed to said portion of said stopper engagement means.

58. A device for separately storing and subsequently mixing the fluid contents of two containers, said device comprising:

a fluid container constructed to define a first sealed compartment for storing a sterile liquid, said fluid container having flexible walls, an independent medicament container constructed to enclose a second compartment and having an egress opening closed by a sealing barrier;

a portion of said fluid container defining an inlet passageway to said first compartment through said walls and including means for affixing said independent medicament container to said fluid container with the opening of such medicament container disposed to be in communication with said passageway and with said sealing barrier of said medicament container exposed to said passageway, said medicament container being so affixed by said means, and means within said first compartment and manipulatable through said flexible walls for removing said sealing barrier to open said medicament container, said flexible walls being of a material and construction such that said walls are deformable inwardly for manipulation of said removing means through said walls for so removing said sealing barrier, whereby a medicament will flow from said medicament container into said first compartment through said passageway.

59. The device as in claim 58 wherein said sealing barrier is a removable stopper and said removing means includes means for removal of said stopper.

60. The device as in claim 58 including a removable element sealing said inlet passageway; said removable element, said sealing barrier and said removing means being joined together whereby said removable element and said sealing barrier may be removed by such manipulation of said removing means to open said inlet passageway and said medicament container.

61. A fluid container for holding a fluid and receiving a medicament thereinto from an independent medicament container having an egress opening closed by a removable sealing barrier, said fluid container constructed to define a sealed compartment for storing a sterile liquid, said fluid container having flexible walls, a portion of said fluid container defining an inlet passageway to said compartment, a sealing barrier enclosing said passageway, means on said fluid container for affixing such an independent medicament container to said fluid container with the opening of said medicament container disposed to be in communication with said passageway and with said sealing barrier of said medicament container exposed to said compartment through passageway, and means within said compartment and manipulatable through said flexible walls for removing both said sealing barrier of said passageway and said sealing barrier of a medicament container so affixed by said affixing means to open such an affixed medicament container and said passageway, said flexible walls being of a material and construction such that said walls are deformable inwardly for manipulation of said removing means through said walls for so removing said sealing barrier, whereby a medicament will flow from such an affixed medicament container into said compartment through said passageway.

62. A fluid container for holding a fluid and receiving a medicament thereinto from an independent medicament container having an egress opening closed by a removable stopper, said fluid container constructed to define a sealed compartment for storing a sterile liquid, said fluid container having flexible walls, a portion of said fluid container defining an inlet passageway to said compartment, a sealing barrier closing said passageway, means on said fluid container for affixing such an independent medicament container to said fluid container with the opening of such medicament container disposed to be in communication with said passageway and with said stopper of said medicament container exposed to said compartment through passageway, means within said compartment and manipulatable through said flexible walls for removal of said sealing barrier, said flexible walls being of a material and construction such that said walls are deformable inwardly for manipulation of said removal means through said walls for so removing said sealing barrier, means for removal of the stopper of such a medicament container so affixed by said affixing means upon removal of said sealing barrier, to thereby open both such an affixed medicament container and said passageway, whereby a medicament will flow from such an affixed medicament container into said compartment through said passageway.

63. A fluid container as defined in claim 62 wherein said affixing means includes a port member in sealing engagement with said flexible container walls and defining said inlet passageway therethrough.

64. A fluid container as defined in claim 63 wherein said port member includes a sleeve and a cap for forming a sealed enclosure over such a medicament container.

65. A fluid container as defined in claim 63 wherein said port member is of a configuration to receive therein at least the end portion of such a medicament container adjacent said opening therein, and including means for effecting sealing engagement between such an end portion around said opening and the portion of said fluid container around said inlet passageway.

66. A fluid container as defined in claim 65 and including screw threads in said port for engaging complementary screw threads on such a medicament container.

67. A fluid container as defined in claim 62 including means for effecting sealing engagement between an end portion of such an attached container around said opening therein and the portion of said fluid container around said passageway.

68. A fluid container as defined in claim 63 wherein said sealing barrier of said passageway comprises a removable cover sealing the inner end of said port member.

69. A fluid container as defined in claim 68 wherein said port member extends into said flexible container, and means attached to said cover for manual engagement through said walls for removing said cover.

70. A fluid container as in claim 69 and including means attached to said cover for engaging a removable stopper in a medicament container so affixed by said affixing means and withdrawing such a stopper as said cover is removed.

71. A fluid container as in claim 63 and including a removable cover closing the outer end of said port member.

72. A fluid container as in claim 63 wherein said flexible container is formed of two sheets of flexible material sealed to one another at their edges and having respective edge portions sealed to said port member to effect sealed connection therewith.

73. A fluid container as in claim 72 wherein the edge portions of said fluid container define arcuate shoulders and inwardly tapering longitudinal seams on either side of said port member to facilitate flexing of said walls for manipulation of said manipulatable means therethrough.

74. The device as defined in claim 23 or 20 wherein said member is a port in sealing relation with said sides or wall means, respectively.

75. The device as defined in claim 23 or 74 wherein said member includes a sleeve and cap forming a sealed enclosure over said second container.

76. The device as defined in claim 1, 2, 4 or 5 wherein said stopper is resilient and said connection means of said stopper includes a recess in said stopper defining an internal shoulder for receiving in said recess a connecting portion of such a stopper engaging means for engagement over said internal shoulder to effect such removal.

77. A fluid container as defined in claim 65 or 67 wherein said affixing means includes flange means for interlocking engagement with complementary means on a medicament container.

78. A fluid container as defined in claim 65 or 67 wherein said affixing means includes screw threads for engaging complementary screw threads on such a medicament container.

79. A fluid container as in claim 78 including a removable cover closing the outer end of said port member.

80. A fluid container as in claim 68, 69 or 70 including a removable cover closing the outer end of said port member.

81. The invention as defined in claim 58, 59, 60, 6, 61, 62, 63, 64, 65, 66, 67, 68, 69, 70, 71 or 72 wherein said fluid container is readily deformable and of a configuration whereby said portion defining an inlet passageway is movable inwardly and outwardly of said compartment of said fluid container by the user for such manipulation of said means for removing said barrier, barriers and stopper, respectively.

82. The device as defined by claim 7, 8, 10, 11, 12, 13, 14, 15, 16, 17, 9, 19, 42, 43, 44 or 45 wherein said flexible container is readily deformable and of a configuration whereby said second container is movable inwardly and outwardly relative to said flexible container by the user for such manipulation of said means for removing said stopper.

83. The invention as defined in claim 23, 24, 25, 26, 27, 28, 29, 30, 31, 32, 33, 34, 35, 36, 37, 38, 39, or 20 wherein said flexible container is readily deformable and of a configuration whereby said member is movable inwardly and outwardly relative to said compartment of said flexible container by the user for such manipulation of said means for removing said stopper.

84. The invention as defined in claim 46, 47, 49, 51, 54, 55, 48, 50, 52, 53, 57 or 56 wherein said first container is readily deformable and of a configuration whereby said one of said ports is movable inwardly and outwardly relative to said compartment of said first container by the user for such manipulation of said stopper engagement means for removing said stopper.

85. A method of combining a medicament with a diluent comprising the steps of:

providing a medicament in a first container having an egress opening closed by a stopper which is removable by being withdrawn from said opening;

providing a diluent container having flexible walls and an inlet passageway through said walls, said diluent container defining a sealed compartment having therein a fluid diluent and means for engaging the stopper of such a medicament container;

attaching said medicament container to a wall of said diluent container with said egress opening and stopper exposed inwardly of said sealed compartment through said passageway and with said means engaging said stopper;

moving said second container and related portions of said walls inwardly of said compartment by deforming said container walls;

grasping said stopper engaging means through said flexible walls; and retracting said second container and related wall portions of said first container while holding said stopper engaging means to effect withdrawal of said stopper and allow said medicament to flow through said opening into said diluent in said sealed compartment.

86. A method of combining a medicament with a diluent comprising the steps of:

providing a medicament in a first container having an egress opening closed by a stopper which is removable by being withdrawn from said opening;

providing a diluent container having flexible walls and an inlet port through said walls with a sealing closure on the inner end of said port, said diluent container defining a sealed compartment having therein a fluid diluent, and means on said sealing closure for engaging the stopper of such a medicament container;

inserting said medicament container into said port with said egress opening and stopper exposed inwardly of said sealed compartment and thereby engaging said stopper on said stopper engaging means;

moving port and said second container and related portions of said walls inwardly of said compartment by deforming said container walls;

grasping said sealing closure through said flexible walls; and retracting said second container and related wall portions of said first container while holding said sealing closure to effect removal of said sealing closure and withdrawal of said stopper and allow said medicament to flow through said opening into said diluent in said compartment.

* * * * *

UNITED STATES PATENT AND TRADEMARK OFFICE

CERTIFICATE OF CORRECTION

PATENT NO. : 4,614,267

DATED : September 30, 1986

INVENTOR(S) : Mark E. Larkin

It is certified that error appears in the above-identified patent and that said Letters Patent is hereby corrected as shown below:

Col. 5, l. 17, after "protrusion" insert --540. In this manner cover 542 is retained on sleeve--. Col. 12, l. 7, "20" should read --30--. Col. 15, claim 18, l. 27, insert a comma "," after --container--. Col. 17, claim 41, l. 17, delete "first." Col. 18, claim 47, ll. 27, 28 "engagement" should read --engaging--. Col. 18, claim 49, ll. 40, 41 "engagement" should read --engaging--. Col. 18, claim 51, ll. 53, 58 "engagement" should read --engaging--. Col. 19, claim 54, ll. 2, 8, "engagement" should read --engaging--. Col. 19, claim 55, ll. 13, 19, "engagement" should read --engaging--. Col. 19, claim 56, l. 24, "engagement" should read --engaging--. Col. 19, claim 57, ll. 31, 36, 42, "engagement" should read --engaging--. Col. 20, claim 61, l. 23, "enclosing" should read --closing--. Col. 20, claim 61, l. 26, "said" should read --such--. Col. 20, claim 62, l. 61, after "through" insert --said--. Col. 22, claim 84, l. 45, "engagement" should read --engaging--. Col. 24, claim 86, l. 6, after "moving" insert --said--.

Signed and Sealed this

Twenty-fourth Day of March, 1987

*Attest:*

DONALD J. QUIGG

*Attesting Officer*

*Commissioner of Patents and Trademarks*